United States Patent
Rentschler et al.

(10) Patent No.: US 11,179,027 B2
(45) Date of Patent: Nov. 23, 2021

(54) ENDOSCOPIC DEVICES AND METHODS USING SAME

(71) Applicant: THE REGENTS OF THE UNIVERSITY OF COLORADO, A BODY CORPORATE, Denver, CO (US)

(72) Inventors: Mark Rentschler, Boulder, CO (US); Levin J. Sliker, Boulder, CO (US); Madalyn D. Kern, Broomfield, CO (US); Joseph Micah Prendergast, Boulder, CO (US); William S. Smith, Boulder, CO (US); Kyle Galbraith, Santa Rosa, CA (US); James Depoy, Parker, CO (US); Karina Rose Laguardia, Boulder, CO (US); Andrew Patrick Gloor, Salida, CO (US); Derek Sawyer, Colorado Springs, CO (US)

(73) Assignee: The Regents of the University of Colorado, a Body Corporate, Denver, CO (US)

( * ) Notice: Subject to any disclaimer, the term of this patent is extended or adjusted under 35 U.S.C. 154(b) by 492 days.

(21) Appl. No.: 15/780,493

(22) PCT Filed: Dec. 5, 2016

(86) PCT No.: PCT/US2016/064915
§ 371 (c)(1),
(2) Date: May 31, 2018

(87) PCT Pub. No.: WO2017/096350
PCT Pub. Date: Jun. 8, 2017

(65) Prior Publication Data
US 2018/0368665 A1 Dec. 27, 2018

Related U.S. Application Data

(60) Provisional application No. 62/263,640, filed on Dec. 5, 2015.

(51) Int. Cl.
*A61B 1/00* (2006.01)
*A61B 1/31* (2006.01)
*A61M 25/10* (2013.01)

(52) U.S. Cl.
CPC ...... *A61B 1/00154* (2013.01); *A61B 1/00082* (2013.01); *A61B 1/00135* (2013.01); *A61B 1/31* (2013.01); *A61M 25/1011* (2013.01)

(58) Field of Classification Search
CPC ............ A61B 1/00154; A61B 1/00082; A61B 1/00135; A61B 1/31; A61M 25/1011
See application file for complete search history.

(56) References Cited

U.S. PATENT DOCUMENTS

| 4,364,392 A | 12/1982 | Strother et al. |
| 6,120,516 A | 9/2000 | Selmon et al. |

(Continued)

FOREIGN PATENT DOCUMENTS

| JP | 3799612 B2 | 7/2006 |
| WO | 2015065163 A1 | 5/2015 |

(Continued)

OTHER PUBLICATIONS

International Search Report & Written Opinion for corresponding International Application No. PCT/US2016/064915.

(Continued)

*Primary Examiner* — Timothy J Neal
*Assistant Examiner* — William B Chou
(74) *Attorney, Agent, or Firm* — Polsinelli PC

(57) ABSTRACT

The invention provides devices that can be used for any endoscopy procedure. In certain embodiments, the devices of the invention reduce the occurrence of looping in the most difficult segment of the colon to navigate—the splenic flexure. In other embodiments, the devices of the invention make colonoscopies more comfortable for patients and (Continued)

reduce the risk of damage to the colon. In yet other embodiments, the devices of the invention comprise a supportive, friction-reducing device that can be attached to the tip of existing endoscopes to help the scope advance better through the colon and intestinal tract.

20 Claims, 25 Drawing Sheets

(56) References Cited

U.S. PATENT DOCUMENTS

| | | | |
|---|---|---|---|
| 6,258,099 B1 | 7/2001 | Mareiro | |
| 6,478,807 B1 | 11/2002 | Foreman et al. | |
| 6,676,667 B2 | 1/2004 | Mareiro et al. | |
| 6,835,189 B2 | 12/2004 | Musbach et al. | |
| 6,841,213 B2 | 1/2005 | Parsonage et al. | |
| 7,306,616 B2 | 12/2007 | Eidenschink et al. | |
| 7,354,419 B2 | 4/2008 | Davies, Jr. et al. | |
| 7,459,192 B2 | 12/2008 | Parsonage et al. | |
| 7,776,078 B2 | 8/2010 | Burgmeier et al. | |
| 7,927,362 B2 | 4/2011 | Shippy, III et al. | |
| 7,963,942 B2 | 6/2011 | Chen | |
| 7,985,063 B2 | 7/2011 | Schewe et al. | |
| 8,048,028 B2 | 11/2011 | Horn et al. | |
| 8,048,093 B2 | 11/2011 | Mapes et al. | |
| 8,096,942 B2 | 1/2012 | Yoshida et al. | |
| 8,202,245 B2 | 6/2012 | Weber et al. | |
| 8,216,267 B2 | 7/2012 | Pallazza | |
| 8,353,868 B2 | 1/2013 | Davies, Jr. et al. | |
| 8,550,985 B2 | 10/2013 | Weber et al. | |
| 8,597,239 B2 | 12/2013 | Gerrans et al. | |
| 8,690,824 B2 | 4/2014 | Holman et al. | |
| 8,771,332 B2 | 7/2014 | Johnson et al. | |
| 8,852,146 B2 | 10/2014 | Horn et al. | |
| 8,876,763 B2 | 11/2014 | Noddin | |
| 8,945,047 B2 | 2/2015 | McAuley et al. | |
| 8,945,168 B2 | 2/2015 | Davies, Jr. et al. | |
| 9,067,045 B2 | 6/2015 | Burton et al. | |
| 9,295,808 B2 | 3/2016 | De Kock et al. | |
| 9,339,169 B2 | 5/2016 | Rentschler et al. | |
| 9,409,001 B2 | 8/2016 | Aggerholm et al. | |
| 9,415,193 B2 | 8/2016 | Campbell et al. | |
| 9,492,297 B2 | 11/2016 | Pallazza | |
| 9,521,945 B2 | 12/2016 | Farhadi | |
| 9,592,119 B2 | 3/2017 | Tilson et al. | |
| 9,717,615 B2 | 8/2017 | Grandt | |
| 9,730,726 B2 | 8/2017 | Bacino et al. | |
| 9,867,529 B2 | 1/2018 | Farhadi | |
| 9,901,715 B2 | 2/2018 | Cully et al. | |
| 9,993,626 B2 | 6/2018 | Lysgaard | |
| 10,166,374 B2 | 1/2019 | Giasolli et al. | |
| 10,173,038 B2 | 1/2019 | Campbell et al. | |
| 10,201,683 B2 | 2/2019 | Schneider et al. | |
| 10,335,581 B2 | 7/2019 | Schneider et al. | |
| 10,376,679 B2 | 8/2019 | Cox et al. | |
| 10,456,564 B2 | 10/2019 | Terliuc et al. | |
| 10,617,853 B2 | 4/2020 | Campbell et al. | |
| 2004/0044351 A1 | 3/2004 | Searle et al. | |
| 2004/0092870 A1 | 5/2004 | Squire | |
| 2005/0137615 A1 | 6/2005 | Mapes et al. | |
| 2007/0106216 A1 | 5/2007 | Noddin | |
| 2007/0112250 A1* | 5/2007 | Kura | A61B 1/05 600/114 |
| 2008/0228139 A1 | 9/2008 | Melsheimer | |
| 2008/0269559 A1 | 10/2008 | Miyamoto et al. | |
| 2009/0125037 A1* | 5/2009 | Goto | A61B 1/00087 606/140 |
| 2010/0022832 A1 | 1/2010 | Makiyama et al. | |
| 2010/0240955 A1* | 9/2010 | Sinai | A61M 25/0105 600/116 |
| 2010/0318094 A1 | 12/2010 | Oishi et al. | |
| 2011/0105840 A1* | 5/2011 | Terliuc | A61B 1/00082 600/104 |
| 2011/0251458 A1* | 10/2011 | Terliuc | A61B 1/31 600/116 |
| 2012/0323074 A1* | 12/2012 | Iyama | A61B 1/015 600/114 |
| 2014/0276407 A1 | 9/2014 | Devries et al. | |
| 2015/0057657 A1 | 2/2015 | Squire et al. | |
| 2015/0088246 A1* | 3/2015 | Astarci | A61B 17/320725 623/2.11 |
| 2016/0058982 A1 | 3/2016 | Aggerholm et al. | |
| 2017/0156571 A1* | 6/2017 | Liu | A61B 1/00135 |
| 2017/0333686 A1 | 11/2017 | Schneider et al. | |
| 2018/0140804 A1 | 5/2018 | Tsukamoto et al. | |
| 2018/0256863 A1 | 9/2018 | Lysgaard | |
| 2018/0304052 A1 | 10/2018 | Schneider et al. | |
| 2019/0216297 A1 | 7/2019 | Rentschler et al. | |
| 2020/0178773 A1* | 6/2020 | Miller | A61B 1/00096 |

FOREIGN PATENT DOCUMENTS

| | | |
|---|---|---|
| WO | WO 2015/065163 A1 | 5/2015 |
| WO | WO 2018/143254 A1 | 8/2018 |

OTHER PUBLICATIONS

Extended European Search Report, EP16871700.7, dated Jul. 5, 2019.

International Search Report and Written Opinion, PCT/US2016/064915, dated Apr. 13, 2017.

International Search Report and Written Opinion, PCT/US2019/013832, dated Apr. 10, 2019.

Non-Final Office Action, U.S. Appl. No. 16/249,550, dated Jun. 26, 2020.

\* cited by examiner

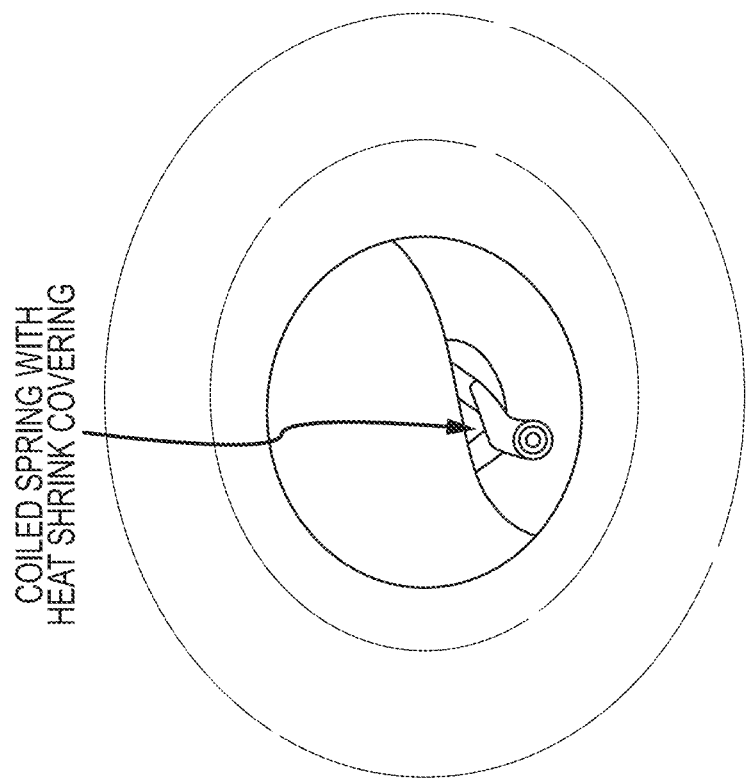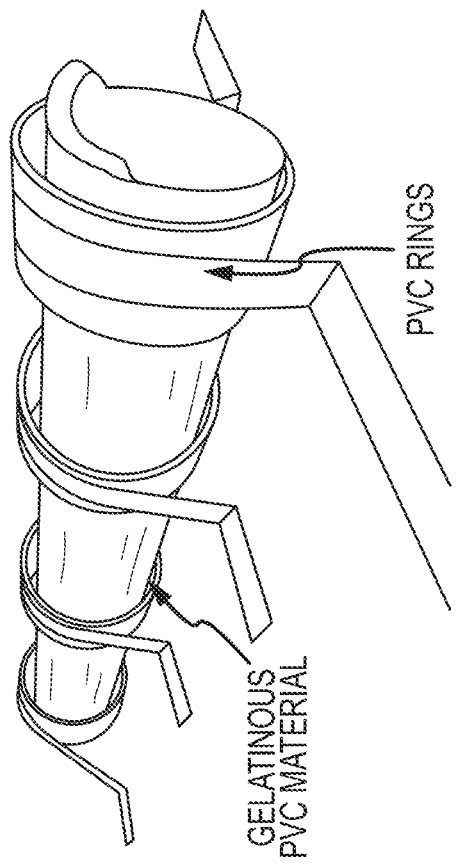
FIG. 2

FIG. 18A

```
// Advanced Medical Technologies Laboratory
// Senior Design Project - Team #2
// April 22, 2015
// Syringe Pump Control R8
// Added potentiometer for volume variability, debounce function for foot pedal // Direct questions to Andrew Gloor - apgloor1@gmail.com // Variable Initialization
int pwm_outer = 3;
//PWM control for motor outputs 1 and 2 is on digital pin 3
int pwm_inner = 11;
//PWM control for motor outputs 3 and 4 is on digital pin 11
int dir_outer = 12;
//dir control for motor outputs 1 and 2 is on digital pin 12
int dir_inner = 13;
//dir control for motor outputs 3 and 4 is on digital pin 13
int Inflate = LOW;
int Deflate = HIGH;
int speed_avg = 150;
//Can be adjusted to change actuator speed. Between 0 and 255.
int pot_outer = 0;
int pot_inner = 1;
int pot_vol = 2;
int potval_outer = 0;
int potval_inner = 0;
int potval_vol = 0;
int startval = 0;
int pedalpin = 10;
int startpin = 9;
int pedalReading = 0;
int pedalState = LOW;
int lastPedalState = LOW;
int n = 0;
```

FIG. 18B

```
int m = 0;

long lastDebounceTime = 0;
long debounceDelay = 50;

// Assign pin controls
void setup(){
pinMode(pwm_outer, OUTPUT); //Set control pins to be outputs
pinMode(pwm_inner, OUTPUT);
pinMode(dir_outer, OUTPUT);
pinMode(dir_inner, OUTPUT);
pinMode(pedalpin, INPUT);
pinMode(startpin, INPUT);
digitalWrite(dir_outer, Inflate); //Set motor direction, 1 low, 2 high
digitalWrite(dir_inner, Inflate); //Set motor direction, 3 high, 4 low
//analogWrite(pwm_outer,speed_avg);
//analogWrite(pwm_inner,speed_avg);
delay(1000);
Serial.begin(9600);
} void loop(){
// Read pot values
pedalReading = digitalRead(pedalpin); // Either HIGH or LOW
startval = digitalRead(startpin);
potval_outer = analogRead(pot_outer);
potval_inner = analogRead(pot_inner);
potval_vol = analogRead(pot_vol);
if (m == 0){
  deflateALL();
   // Ensure that linear actuators are in proper start position.
// Note: Air lines should be connected to the syringe pump
// AFTER it is connected to power.
}
  // When Begin/End switch is flipped, either inflate or deflate
  // inner balloon.
  if (startval == HIGH){
```

FIG. 18C

```
    if (m == 0){ // i.e. overtube has not yet been fixed to the scope
      beginProcedure();
       // Inflate inner balloon. See functions at bottom of script.
      delay(1000);
      m = 1; // Record that inner ballon is inflated.
    }
    else{
      endProcedure();
      delay(1000);
      m = 0;
    }
  }
if (m == 1){ // If inner balloon has been inflated...
  if (pedalReading != lastPedalState)
   { // If the foot pedal state has changed...
      lastDebounceTime = millis(); // Record the time.
  }
  if ((millis() - lastDebounceTime) > debounceDelay)
   { // If the foot pedal has changed after a long enough time with
//no change...
    if (pedalReading != pedalState)
     { // If the current pedal reading is different from the
//previous accepted pedal state...
       pedalState = pedalReading; // Change the pedal state.
       if (pedalState == HIGH)
        { // If the pedal is pressed...
         if (n%2 == 0){ // Alternate between inflation
         //and deflation functions...
           inflate();
         }
         if (n%2 ==1){
           deflate();
         }
         n++;
       }
     }
   }
 }
lastPedalState = pedalReading; // Update the current pedal state.
```

//////////////////////////////////////////////////////
// FUNCTIONS FOR PUMP TO EXECUTE BASED ON STATE //
//////////////////////////////////////////////////////

// Initialize procedure by inflating inner balloon
void beginProcedure(){
  // While the actuator position is short of the established
  inflated position, inflate the inner balloon.
  while (potval_inner < 800)
  { // Pot readings range between 0 and 1023.
  //For inner balloon, the actuator position at
  //potval_inner=800 was found to give an ideal amount of
  //inflation if potval_inner=550 in the deflated position.
     digitalWrite(dir_inner, Inflate);
     analogWrite(pwm_inner, speed_avg);
     potval_inner = analogRead(pot_inner);
  }
  analogWrite(pwm_inner, 0);
}

// End procedure by deflating inner balloon
void endProcedure(){
  // While the actuator position is past the deflated position,
  //deflate inner balloon.
  while (potval_inner > 550){
     digitalWrite(dir_inner, Deflate);
     analogWrite(pwm_inner, speed_avg);
     potval_inner = analogRead(pot_inner);
  }
  analogWrite(pwm_inner, 0);
}

// Inflate outer balloon and deflate inner balloon
void inflate(){
  // Inflate the outer balloon until it reaches the desired volume,
```

FIG. 18E

```
  //and then deflate the inner balloon.
  while (potval_outer < (potval_vol*0.587+200)){ // Equation is based
  //on the maximum and minimum output values for the
  //slide pot, related to the maximum and minimum desired volume
  //of the outer balloon.
    digitalWrite(dir_outer, Inflate);
    analogWrite(pwm_outer,speed_avg);
    potval_outer = analogRead(pot_outer);
    potval_vol = analogRead(pot_vol);
  }
  analogWrite(pwm_outer,0);
  while (potval_inner > 550){
     digitalWrite(dir_inner, Deflate);
     analogWrite(pwm_inner, speed_avg);
     potval_inner = analogRead(pot_inner);
  }
  analogWrite(pwm_inner, 0);
}

// Deflate outer balloon and inflate inner balloon
void deflate(){
  // Inflate the inner balloon, and then deflate the outer balloon.
  while (potval_inner < 800){
    digitalWrite(dir_inner, Inflate);
    analogWrite(pwm_inner, speed_avg);
    potval_inner = analogRead(pot_inner);
  }
  analogWrite(pwm_inner, 0);
  while (potval_outer > 100){
    digitalWrite(dir_outer, Deflate);
    analogWrite(pwm_outer,speed_avg);
    potval_outer = analogRead(pot_outer);
  }
  analogWrite(pwm_outer,0);
}

// Deflate all balloons
void deflateALL(){
```

FIG. 18F

```
while (potval_outer > 100){
   digitalWrite(dir_outer, Deflate);
   analogWrite(pwm_outer,speed_avg);
   potval_outer = analogRead(pot_outer);
}
analogWrite(pwm_outer,0);
while (potval_inner > 550){
    digitalWrite(dir_inner, Deflate);
    analogWrite(pwm_inner, speed_avg);
    potval_inner = analogRead(pot_inner);
}
analogWrite(pwm_inner, 0);
}
```

ENDOSCOPIC DEVICES AND METHODS USING SAME

CROSS-REFERENCE TO RELATED APPLICATIONS

The present application is a 35 U.S.C. § 371 national phase application of, and claims priority to, International Application No. PCT/US2016/064915, filed Dec. 5, 2016, which claims priority under 35 U.S.C. § 119(e) to U.S. Provisional Application No. 62/263,640, filed Dec. 5, 2015, all of which applications are incorporated herein by reference in their entireties.

STATEMENT REGARDING FEDERALLY SPONSORED RESEARCH OR DEVELOPMENT

This invention was made with government support under grant number CMMI 1235532 awarded by the National Science Foundation. The government has certain rights in the invention.

BACKGROUND OF THE INVENTION

Colorectal cancer is the third most common type of cancer in both men in women with over 130,000 cases expected to be diagnosed in 2014. With an estimated 50,000 deaths expected from colorectal cancer in the United States in 2014, it is also one of the most deadly cancers. The five year survivability of colorectal cancer is only 65%. However, with early detection of the cancer, the five year survivability can rise up to as high as 90%. Currently, only about 40% of cases of colorectal cancer are detected at an early enough stage, which makes regular screenings for early detection important. Screenings allow for the detection and removal of colon polyps that could be potentially cancerous at early stages when treatment is less invasive and has a much higher survivability.

The most common method of screening for colorectal cancer is by colonoscopy, which is a procedure that allows a doctor to examine the colon using a thin flexible tube called an endoscope. This tool has a camera, light source and tools on the end for the doctor to treat any signs of cancerous polyps that they may see during the screening. Colonoscopies are performed by inserting the endoscope into the colon and is moved using the push force applied by the doctor. The scope then pushes against the wall of the colon until the colon provides a counter-force on the scope, allowing for it to bend with the curve of the organ. Due to the pliable nature of the tissue in the colon, a colonoscopy can be a difficult procedure to perform, and therefore requires specialized doctors with extensive training and expertise.

As the scope progresses through the colon, frictional forces build up along its length, making it more difficult to advance through the colon. Sometimes, this frictional force is so great that, while the doctor proceeds to insert further sections of the scope into the patient, the tip may not be moving. This event is known as looping, and can cause severe discomfort in the patient, and in some cases can cause a perforation in the colon wall, which would require immediate emergency surgery.

There is thus a need in the art for novel devices that can be attached to the tip of an colonoscope/endoscope and reduce the occurrence of looping during colonoscopies. Such devices should increase the amount of successful completions of colonoscopy procedures, and provide a more comfortable experience for the patient. By allowing for more colonoscopies to be completed fully, more cases of colorectal cancer could potentially be found in early enough stages for successful treatment. The present invention fulfills this need.

BRIEF SUMMARY OF THE INVENTION

The invention provides an endoscopic device. The invention further provides a method of performing endoscopy in a body cavity.

In certain embodiments, the device comprises a flexible overtube that is adapted to fit over at least a section of the outer surface of an endoscope. In other embodiments, the device comprises a first inflatable balloon that is attached to the inner surface of the overtube, whereby, upon insertion of an endoscope within the overtube, the first inflatable balloon surrounds at least a section of the endoscope and is located inbetween the overtube and the endoscope. In yet other embodiments, the device comprises at least one second inflatable balloon that is attached to the outer surface of the overtube, whereby, upon insertion of an endoscope within the overtube, the at least one second inflatable balloon at least partially surrounds at least a section of the overtube and at least a section of the endoscope.

In certain embodiments, the device further comprises an endoscope. In other embodiments, the endoscope is inserted into the overtube. In yet other embodiments, the first inflatable balloon surrounds at least a section of the endoscope and is located inbetween the overtube and the endoscope. In yet other embodiments, the at least one second inflatable balloon at least partially surrounds at least a section of the overtube and at least a section of the endoscope.

In certain embodiments, the device further comprises a first tubing that is in fluid communication with the first inflatable balloon and a second tubing that is in fluid communication to the at least one second inflatable balloon. In other embodiments, the first and second tubings allow for independent inflation and/or deflation of the balloons with a fluid.

In certain embodiments, the first and second tubings are independently attached to the outer or inner surface of the overtube. In other embodiments, the first and second tubings are independently in fluid communication with at least one pump system. In yet other embodiments, the at least one pump system is located in the overtube or is external to the endoscopic device. In yet other embodiments, the first and second tubings are independently fillable with a gas or a fluid. In yet other embodiments, the first and second tubings are independently fillable with air. In yet other embodiments, the first inflatable balloon is made of at least one material selected from the group consisting of polydimethylsiloxane (PDMS), LDPE, latex, pebax, silicon, polyethylene terephthalate (PET or PETE), nylon, polyurethane and any other thermoplastic elastomers. In yet other embodiments, the at least one second inflatable balloon is made of at least one material selected from the group consisting of PDMS, LDPE, latex, pebax, silicon, PET, nylon, polyurethane and any other thermoplastic elastomers. In yet other embodiments, the outer surface of the first inflatable balloon and the outer surface of the at least one second inflatable balloon independently comprise friction elements. In yet other embodiments, the friction elements comprise micropatterned structures. In yet other embodiments, the first inflatable balloon and the at least one second inflatable balloon are independently optionally at least partially filled with granular packing. In yet other embodiments, the at least partially granular packing filled balloon(s) is(are) further independently fillable with a fluid.

In certain embodiments, the device further comprises an end cone. In other embodiments, the end cone surrounds at least a section of the outer surface of the endoscope. In yet other embodiments, the end cone is located inbetween the tip (distal extremity) of the endoscope and the at least one second inflatable balloon. In yet other embodiments, one edge of the end cone is positioned next to the at least one second inflatable balloon and has substantially the same diameter as the inflated at least one second inflatable balloon. In yet other embodiments, the other edge of the end cone has substantially the same diameter as the endoscope. In yet other embodiments, inflating the first inflatable balloon anchors the overtube to the endoscope.

In certain embodiments, the method comprises introducing in the body cavity at least a portion of the distal extremity of an endoscopic device of the invention. In other embodiments, the endoscopic device comprises an endoscope to which distal extremity are attached means for examining the body cavity. In yet other embodiments, the endoscopic device comprises a flexible overtube that fits over at least a section of an endoscope's outer surface. In yet other embodiments, the endoscopic device comprises a first inflatable balloon that is attached to the inner surface of the overtube, wherein the first inflatable balloon surrounds at least a section of the endoscope, is located inbetween the overtube and the endoscope, and is at least partially inflated. In yet other embodiments, the endoscopic device comprises at least one second inflatable balloon that is attached to the outer surface of the overtube, wherein the at least one second inflatable balloon at least partially surrounds at least a section of the overtube and at least a section of the endoscope.

In certain embodiments, if insertion of the endoscopic device into the body cavity is met with resistance, the first inflatable balloon is at least partially deflated and the at least one second inflatable balloon is at least partially inflated. In other embodiments, the first and second tubings are independently attached to the outer surface of the overtube.

In certain embodiments, the first inflatable balloon is made of at least one material selected from the group consisting of PDMS, LDPE, latex, pebax, silicon, PET, nylon, polyurethane and any other thermoplastic elastomers.

In certain embodiments, the at least one second inflatable balloon is made of at least one material selected from the group consisting of PDMS, LDPE, latex, pebax, silicon, PET, nylon, polyurethane and any other thermoplastic elastomers.

In certain embodiments, the first inflatable balloon and the at least one second inflatable balloon are independently optionally at least partially filled with granular packing. In other embodiments, the at least partially granular packing filled balloon(s) is(are) further independently fillable with a fluid. wherein the at least partially granular packing filled balloon(s) adopts the shape of the granular packing filling once the fluid is removed from the balloon(s).

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 2 is an exemplary illustration of a simulated test colon.

FIG. 12A illustrates a rendering of the overtube end cone. FIG. 12B illustrates a rendering of the end cone on the scope.

FIG. 16A: plain scope. FIG. 16B: scope with balloon attachment.

FIGS. 18A-18F illustrate an Arduino schematic.

DETAILED DESCRIPTION OF THE INVENTION

Figure 1:
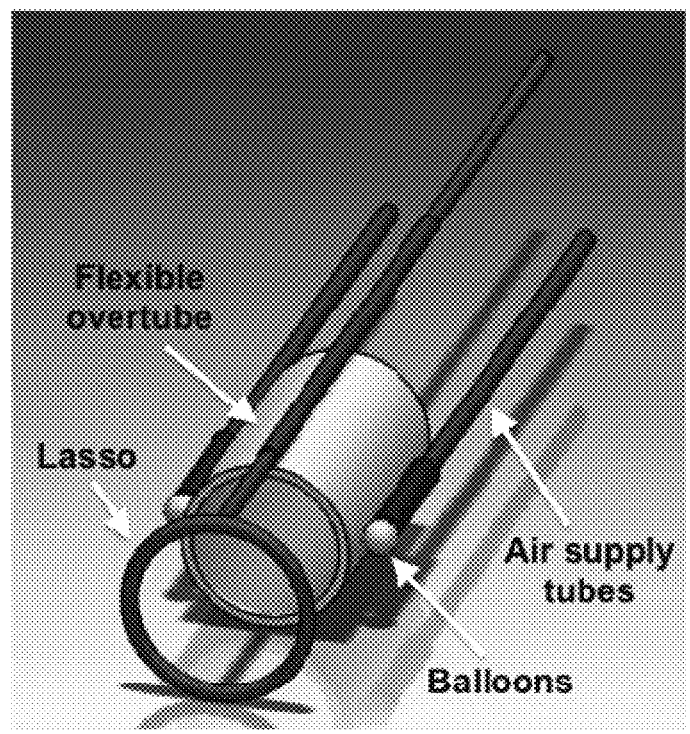
FIG. 1 is an exemplary illustration of a support balloon device.

The invention relates to the unexpected discovery of novel devices that can be attached to an endoscope and allow for reduction in the occurrence of looping during operation of the endoscope in a colonoscopy procedure.

In certain embodiments, the endoscopic or colonoscopic devices of the invention comprises a novel overtube that can be used with any commercially available endoscope/colonoscope to ease insertion, manipulation, and retraction of an endoscope during colonoscopy upper gastrointestinal (GI) tract endoscopy, gastric endoscopy, or small bowel endoscopy. In other embodiments, the device of the invention comprises at least two separate air bladders. The first air bladder, which may be referred to as "inner", is located between the overtube and the endoscope, and the second air bladder, which may be referred to as "outer", is located between the endoscope and the colon wall. By inflating the inner air bladder the overtube adheres to the endoscope during insertion. After the endoscope and overtube reach a challenging corner, such as the splenic flexure, the outer air bladder inflates to anchor the overtube to the wall while the inner air bladder is deflated. This allows the endoscope to pass freely along the overtube.

The devices of the invention can be used in endoscopic procedures. An endoscopically deliverable overtube (which may be disposable or reusable) can facilitate access to the proximal colon including challenging polyps in the right colon, can assist with removing foreign bodies from the GI tract, and can be used in small bowel enteroscopy. In a non-limiting example, polyps may be difficult to physically reach, and placing an overtube just distal to the polyp allows one to reach the polyp without losing one's position. For patients with multiple polyps, the overtube may be placed in whatever part of the colon impedes access. The devices of the invention can also be used in stenting, eliminating some emergency issues after iatrogenic perforations. Similarly, esophageal variceal bleeding can be robust and require placement of a cumbersome Sengstaken-Blakemore or Minnesota tube. In those cases, a temporary stent can be held in place by a balloon, optionally anchored by a tether.

As demonstrated herein, as part of the effort to design a device that reduces the push force applied by the medical specialist during enteroscopy and/or colonoscopy, at least two devices were identified. The first was a device comprising a set of free spinning wheels attached to a chassis, which can be secured in segments along the length of the endoscope to reduce the friction of the colonoscopy. The second device comprises balloons attached to a flexible overtube, which can be secured in the turns of the colon and provide support for the scope as the procedure is performed.

In certain embodiments, the device of the invention comprises: a long, flexible overtube to provide support to the endoscope; at least one inflatable balloon on the outside of the overtube to provide structure in the colon; layflat tubing on the inside of the overtube to secure the overtube to the endoscope when it is not secured to the colon; tubing to provide an air supply to the balloons; a syringe pump system to inflate and deflate the balloons. In other embodiments, the devices of the invention reduce friction along the colon walls in the splenic flexure turn during a colonoscopy. By having a flexible overtube that detaches from the scope and inflates a balloon at key turns through the colon, the endoscope can be guided more easily and the force exerted by the endoscope on the colon walls can be better dispersed. This decreases the push force required by the doctor, and helps reduce the occurrence of looping in colonoscopies. Exemplary devices of the invention showed a 37% reduction in average peak push force through the splenic flexure with the overtube device on compared to just the plain endoscope.

The invention contemplates various arrangements for the inner air bladder(s), as well as for the outer air bladder(s), and such arrangements are combinable in any feasible and/or operative manner. In a non-limiting example, the outer air bladder has a toroidal-like (doughnut-like) shape, and its inner circumference fits around the overtube. At least in that case, the outer air bladder surrounds at least a section of the overtube. In another non-limiting example, the outer air bladder does not wrap around the overtube, and instead is located along the surface of at the least a section of the overtube. For example, the outer air bladder can be longitudinally situated along the surface of at the least a section of the overtube, and/or the outer air bladder can be situated along the surface of at the least a section of the overtube at an angle with respect to the overtube axis (i.e., obliquely along the surface of at the least a section of the overtube, at an angle of 15°, 30°, 45°, 60°, 75° or any other angle). At least in those cases, the outer air bladder at least partially surrounds at least a section of the overtube. In certain embodiments, the outer air bladder is located close to the end or edge of the tube. In other embodiments, the outer air bladder is not located close to the end or edge of the tube. In yet other embodiments, the outer air bladder is located along the length of the tube.

The invention further contemplates that one or more outer air bladders are used within the device of the invention. In the case that two or more outer air bladders are present, they can be selected from any type of bladder contemplated herein, and the two or more outer air bladders can be of the same type or can be of distinct types. In certain embodiments, each of the two or more outer air bladders are in fluid communication with separate tubing that allows for independent inflation and/or deflation of the two or more bladders with a fluid. In other embodiments, two or more of the outer air bladders are in fluid communication with a set of tubings that allows for their simultaneous and/or coordinated inflation and/or deflation with a fluid. In other embodiments, all of the outer air bladders are in fluid communication with a set of tubings that allows for their simultaneous and/or coordinated inflation and/or deflation with a fluid.

In certain embodiments, fluid can be used to pressurize the at least one balloon to hold the endoscope tube in place. In other embodiments, friction elements on at least a section of the surface of the balloon are employed to prevent movement of the balloon. Friction elements can be introduced for example by placing micro-patterned structures on the balloon. For example, microstructures can be molded into materials used to make the balloon, such as but not limited to, polydimethylsiloxane (PDMS), latex and/or silicone. In other embodiments, at least a section of the surface of the balloon is coated with a lubricious coating, which may be hydrophilic or hydrophobic. In yet other embodiments, substantially the entire surface of the balloon is coated with a lubricious coating, which may be hydrophilic or hydrophobic. In other embodiments, at least a section of the surface of the tube is coated with a lubricious coating, which may be hydrophilic or hydrophobic. In yet other embodiments, substantially the entire surface of the tube is coated with a lubricious coating, which may be hydrophilic or hydrophobic.

In other embodiments, the balloons are pressurized at least in part using granular packing, so that the balloons may conform to the cavity shape. Such granular packing may be in the form of small rice-shaped grains, spherical grains, or grains of any other shape. In certain embodiments, when a fluid is added to the balloon that already holds granular packing, the balloon becomes more flexible and can be compressed or formed into any number of shapes. Once the fluid is removed from the balloon, the balloon retains the shape imposed by the grains, which are compressed against each other and prevent movement. Such method can be used in certain embodiments to help maintain a desired shape for the tube in any number of regions within the tract.

Compositions

The invention provides an endoscopic device. In certain embodiments, the device comprises a flexible overtube that is adapted to fit over at least a section of the outer surface of an endoscope. In other embodiments, the device comprises a first inflatable balloon that is attached to the inner surface of the overtube, whereby, upon insertion of an endoscope within the overtube, the first inflatable balloon surrounds at least a section of the endoscope and is located inbetween the overtube and the endoscope. In other embodiments, the device comprises at least one second inflatable balloon that is attached to the outer surface of the overtube, whereby, upon insertion of an endoscope within the overtube, the at least one second inflatable balloon at least partially surrounds at least a section of the overtube and at least a section of the endoscope.

In certain embodiments, the device further comprises an endoscope. In other embodiments, the endoscope is inserted into the overtube. In yet other embodiments, the first inflatable balloon surrounds at least a section of the endoscope and is located inbetween the overtube and the endoscope. In yet other embodiments, the at least one second inflatable balloon at least partially surrounds at least a section of the overtube and at least a section of the endoscope.

In certain embodiments, the device further comprises a first tubing that is in fluid communication with the first inflatable balloon and a second tubing that is in fluid communication to the at least one second inflatable balloon, wherein the first and second tubings allow for independent inflation and/or deflation of the balloons with a fluid.

In certain embodiments, the first and second tubings are independently attached to the outer or inner surface of the overtube. In other embodiments, the first and second tubings are independently in fluid communication with at least one pump system. In yet other embodiments, the at least one pump system is located in the overtube or is external to the endoscopic device. In yet other embodiments, the first and second tubings are independently fillable with a gas or a fluid. In yet other embodiments, the first and second tubings are independently fillable with air. In yet other embodiments, the first inflatable balloon is made of at least one material selected from the group consisting of polydimethylsiloxane (PDMS), low-density polyethylene (LDPE), polytetrafluoroethylene (PTFE), polyether ether ketone (PEEK), latex, pebax, silicon, polyethylene terephthalate (PET or PETE), nylon, polyurethane and any other thermoplastic elastomers. In yet other embodiments, the at least one second inflatable balloon is made of at least one material selected from the group consisting of PDMS, LDPE, PTFE, PEEK, latex, pebax, silicon, PET, nylon, polyurethane and any other thermoplastic elastomers.

In certain embodiments, the outer surface of the first inflatable balloon and the outer surface of the at least one second inflatable balloon independently comprise friction elements. In other embodiments, the friction elements comprise micro-patterned structures. In yet other embodiments, the first inflatable balloon and the at least one second inflatable balloon are independently optionally at least partially filled with granular packing. In yet other embodiments, the at least partially granular packing filled balloon(s) is(are) further independently fillable with a fluid.

In certain embodiments, the device further comprises an end cone. In other embodiments, the end cone surrounds at least a section of the outer surface of the endoscope. In yet other embodiments, the end cone is located inbetween the tip (distal extremity) of the endoscope and the at least one second inflatable balloon. In yet other embodiments, one edge of the end cone is positioned next to the at least one second inflatable balloon and has substantially the same diameter as the inflated at least one second inflatable balloon. In other embodiments, the other edge of the end cone has substantially the same diameter as the endoscope.

In certain embodiments, inflating the first inflatable balloon anchors the overtube to the endoscope.

Methods

The invention provides a method of performing endoscopy in a body cavity. In certain embodiments, the method comprises introducing in the body cavity at least a portion of the distal extremity of an endoscopic device. In other embodiments, the endoscopic device comprises an endoscope to which distal extremity are attached means for examining the body cavity. In yet other embodiments, the endoscopic device comprises a flexible overtube that fits over at least a section of an endoscope's outer surface. In yet other embodiments, the endoscopic device comprises a first inflatable balloon that is attached to the inner surface of the overtube, wherein the first inflatable balloon surrounds at least a section of the endoscope, is located inbetween the overtube and the endoscope, and is at least partially inflated. In yet other embodiments, the endoscopic device comprises at least one second inflatable balloon that is attached to the outer surface of the overtube, wherein the at least one second inflatable balloon at least partially surrounds at least a section of the overtube and at least a section of the endoscope.

In certain embodiments, if insertion of the endoscopic device into the body cavity is met with resistance, the first inflatable balloon is at least partially deflated and the at least one second inflatable balloon is at least partially inflated.

In certain embodiments, the device further comprises a first tubing that is in fluid communication with the first inflatable balloon and a second tubing that is in fluid communication to the at least one second inflatable balloon, wherein the first and second tubings allow for independent inflation and/or deflation of the balloons with a fluid.

In certain embodiments, the first and second tubings are independently attached to the outer surface of the overtube. In other embodiments, the first and second tubings are independently in fluid communication with at least one pump system. In yet other embodiments, the first and second tubings are independently fillable with air.

In certain embodiments, the first inflatable balloon is made of at least one material selected from the group consisting of polydimethylsiloxane (PDMS), LDPE, latex, pebax, silicon, polyethylene terephthalate (PET or PETE), nylon, polyurethane and any other thermoplastic elastomers. In other embodiments, the at least one second inflatable balloon is made of at least one material selected from the group consisting of PDMS, LDPE, latex, pebax, silicon, PET, nylon, polyurethane and any other thermoplastic elastomers. In yet other embodiments, the first inflatable balloon and the at least one second inflatable balloon are independently optionally at least partially filled with granular packing. In yet other embodiments, the at least partially granular packing filled balloon(s) is(are) further independently fillable with a fluid. wherein the at least partially granular packing filled balloon(s) adopts the shape of the granular packing filling once the fluid is removed from the balloon(s).

In certain embodiments, the device further comprises an end cone. In other embodiments, the end cone surrounds at least a section of the outer surface of the endoscope. In other embodiments, the end cone is located inbetween the tip (distal extremity) of the endoscope and the at least one second inflatable balloon. In other embodiments, one edge of the end cone is positioned next to the at least one second inflatable balloon and has substantially the same diameter as the inflated at least one second inflatable balloon. In yet other embodiments, the other edge of the end cone has substantially the same diameter as the endoscope.

Definitions

As used herein, each of the following terms has the meaning associated with it in this section.

As used herein, unless defined otherwise, all technical and scientific terms generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element.

As used herein, the term "about" will be understood by persons of ordinary skill in the art and will vary to some extent on the context in which it is used. As used herein, "about" when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the term "instructional material" includes a publication, a recording, a diagram, or any other medium of expression that may be used to communicate the usefulness of the compositions and/or methods of the invention. The instructional material of the kit may, for example, be affixed to a container that contains the compositions of the invention or be shipped together with a container that contains the compositions. Alternatively, the instructional material may be shipped separately from the container with the intention that the recipient uses the instructional material and the compositions cooperatively. For example, the instructional material is for use of a kit; and/or instructions for use of the compositions.

Throughout this disclosure, various aspects of the invention may be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Every formulation or combination of components described or exemplified can be used to practice the invention, unless otherwise stated. Specific names of compounds are intended to be exemplary, as it is known that one of ordinary skill in the art can name the same compounds differently. When a compound is described herein such that a particular isomer or enantiomer of the compound is not specified, for example, in a formula or in a chemical name, that description is intended to include each isomers and enantiomer of the compound described individual or in any combination.

Although the description herein contains many embodiments, these should not be construed as limiting the scope of the invention but as merely providing illustrations of some of the presently preferred embodiments of the invention.

All references throughout this application (for example, patent documents including issued or granted patents or equivalents; patent application publications; and non-patent literature documents or other source material) are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application. In general the terms and phrases used herein have their art-recognized meaning, which can be found by reference to standard texts, journal references and contexts known to those skilled in the art. Any preceding definitions are provided to clarify their specific use in the context of the invention.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials

All materials were used without further preparation unless indicated otherwise below.

Example 1: Devices

The invention relates in part to the development of an endoscope tip device that decreases the necessary push force exerted by doctors through the splenic flexure in colonoscopy procedures. In order to develop a device that effectively solves this problem, certain non-limiting requirements were identified:

(a) Push Force Reduction: the device should reduce the push force necessary to advance a colonoscope through the colonic tract.

(b) Integration with Existing Endoscope: as this device is to function as an attachment to existing endoscope tips, the device's inside diameter must be able to fit around the outer diameter of the endoscope. Typically, endoscopes have an outer diameter of approximately 10-13 mm.

(c) Ease of Use: a single surgeon will operate this device; therefore, controls must be simple and ergonomic.

(d) Length Limit: because this attachment should maneuver around tight corners, the length of the device (or each segment if the device consists of multiple segments) must be limited. In certain embodiments, the maximum length, if rigid, is about 50 mm.
(e) Outer Diameter Limit: as this device can function inside the colonic tract, outside diameter limitations are necessary. In certain embodiments, the device must not have an outer diameter greater than 30 mm.

Example 2: Initial Design

One device of the invention comprises support balloons (FIG. 1). This design comprises a flexible overtube that can be secured onto the endoscope with a lasso. Two balloons are attached to the sides of the overtube and, when inflated, they allow the overtube to remain stationary in a single spot in the colon. The overtube can then be detached from the scope, allowing the scope to move freely through its center. This allows the overtube to provide support and reduce friction in targeted spots of the doctor's choosing, most likely the corners of the colon.

The attachment device for this design (red elements in FIG. 1) comprises a wire loop, or lasso, that, when pulled tight, holds the overtube device to the endoscope. When the scope needs to be able to move through the overtube, the wire loop can be loosened, allowing the scope to disengage. The balloons in this prototype are standard size water balloons (yellow elements in FIG. 1). The majority of each balloon is covered by a small tube (black elements in FIG. 1) to reduce the friction of the balloon on the colon walls before reaching the desired deployment location. The blue tubes are to supply air to the balloons and to guide the lasso from the exterior of the colon.

Testing

After the initial design prototypes were constructed, testing was conducted to help determine if the support balloon device is a viable option for reducing the push force during a colonoscopy. A simulated colon (FIG. 2) made from a gelatinous PVC material was used in this initial testing.

Equipment:
The following equipment was used for testing:
Load Cell: Entran ELPM-T2E-25L; Rated for 25 lbs; 5V excitation voltage.
Simulated Colon (FIG. 2): Gelatinous colon replica—3" OD; PVC rings for structural support.
Simulated Endoscope: Coiled spring from sink snake; Heat shrink covering to increase OD to 10 mm and simulate texture of a real endoscope; Tapped plastic handle to fit load cell.

Procedure:
The following test procedure was executed:
1. Attach colon simulator to bench top in desired position (3 different conditions): Dry test through a straight colon; Dry test through a slight curve in the colon (30° angle); Lubricated test through a slight curve in the colon (30° angle).
2. Attach handle to load cell and then to test endoscope.
3. Attach appropriate scope configuration to the tip of the test endoscope: P lain scope; Support balloons device attached.
4. Begin data acquisition in LabVIEW.
5. Begin pushing the scope through the colon simulator. Advance the scope at a speed of 1 in/sec.
6. When data acquisition ends, save the data in an Excel file.
7. Repeat testing 10 times for each configuration.

Figure 3:
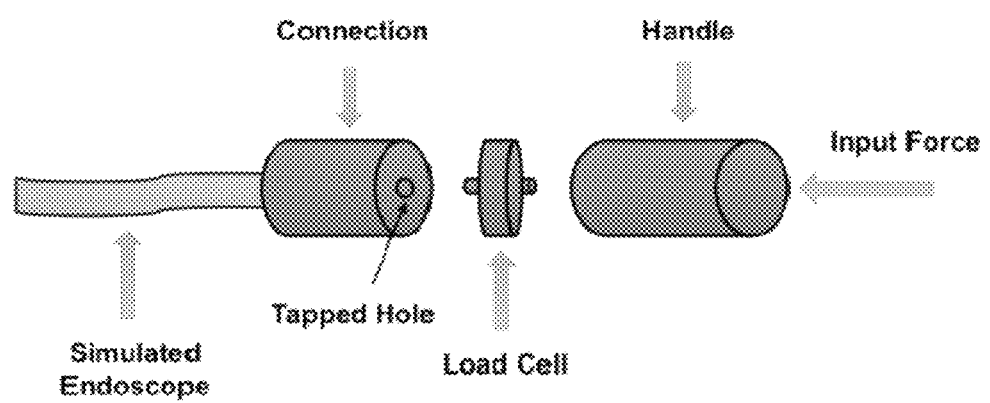
FIG. 3 is an exemplary illustration of a load cell and handle connection.

In order to accurately measure the push force that was applied to the endoscope, a special handle that allowed the load cell to record force data was used. One side of the handle was attached to the back of the test endoscope, with a tapped hole that allowed for the load cell to be attached. Another segment of handle had the same hole tapped and was attached to the other side of the load cell. The tester pushes this back part of the handle in order to have the load cell measure the force applied. A schematic of this load cell handle can be seen in FIG. 3.

Results

From initial testing, it can be seen in Table 1 that force data was taken from the balloon device and scope before and after the balloons were deployed. Before they deployed showed an increase in push force, however, a decrease in the measured push force was observed afterwards. These reported force measurements are an average across all trials.

TABLE 1

Force data collected from the first round of testing

| Test | Device | Before (lbf) | % Diff | After (lbf) | % Diff |
|---|---|---|---|---|---|
| Straight | Plain Scope | 0.63 | — | — | — |
|  | Balloons | 0.88 | +40 | 0.56 | −12 |
| Curved | Plain Scope | 0.77 | — | — | — |
|  | Balloons | 0.51 | +29 | 0.9 | +17 |
| Lubricated + | Plain Scope | 0.27 | — | — | — |
| Curved | Balloons | 0.36 | +33 | 0.25 | −7 |

Uncertainty Analysis

For each test, the largest force measurements were recorded in order to obtain an average maximum push force. Uncertainty in each force measurement due to discretization error and load cell uncertainty u=±0:06 lbf. This value was determined using the specification sheet for the Entran ELPM-T2E-25L load cell.

Performance Assessment

Plain Scope

The plain scope on its own performed well due to the simplicity and small diameter. Without any devices attached, the scope encountered a lot of friction when progressed through the colon simulator. Due to lack of an articulate tip and a greater stiffness than a real scope, maneuverability around corners was near impossible. The tip of the scope pushed against the walls, resulting in a high force concentration.

Balloons

The deployable balloon design dispersed the push force through the corner when deployed. The balloons also reduced the friction in the areas directly before and after the balloon overtube by elevating the scope off the colon walls. Before deployment, the balloons increased the friction force during scope advancement.

Example 3

Figure 4:
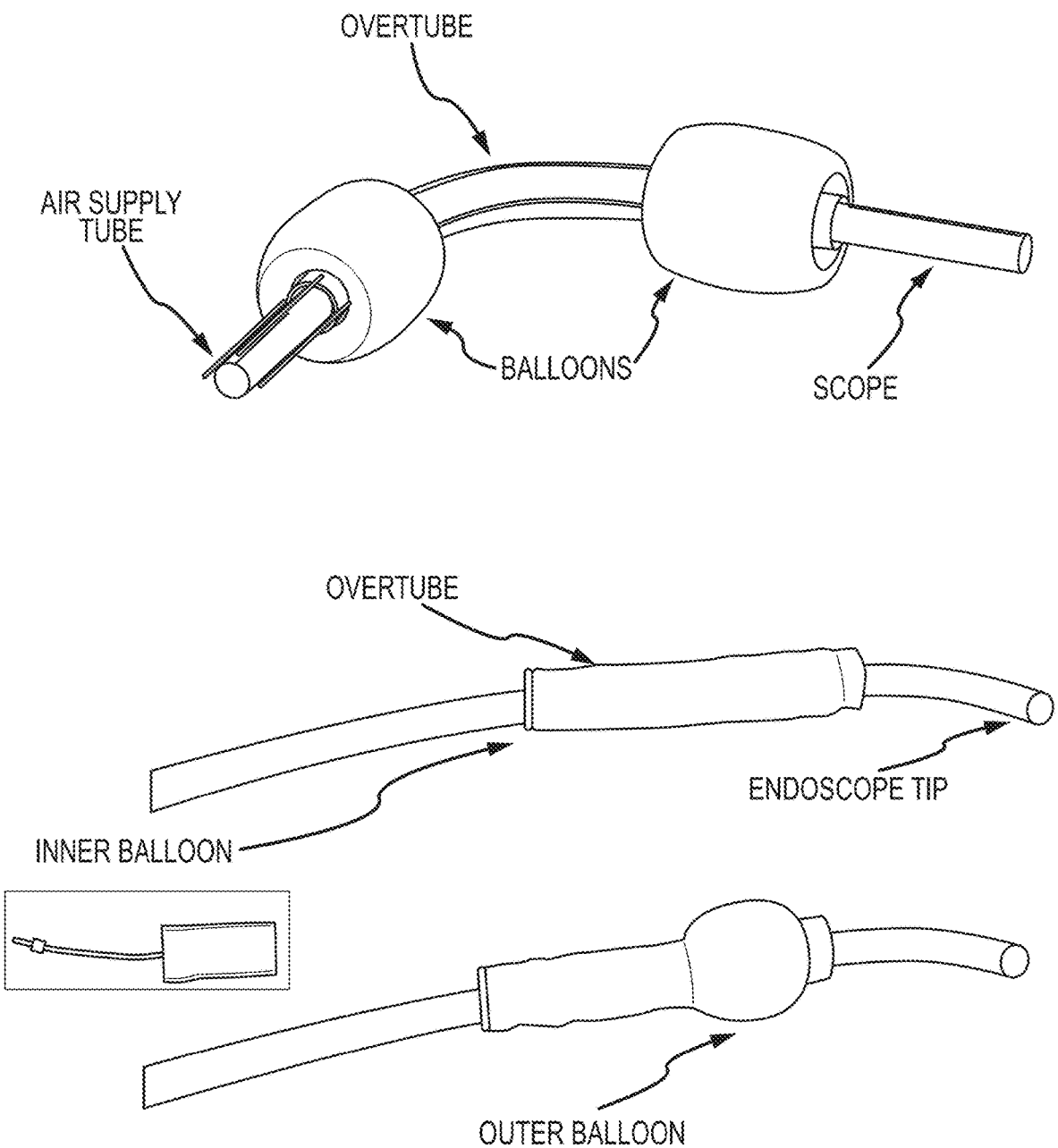
FIG. 4 is exemplary illustrations of non-limiting devices of the invention, comprising a support balloon design with donut-shaped balloons.

The device described elsewhere herein comprised two balloons attached to the sides of an overtube, wherein each balloon had an air supply tube running along the length of the endoscope. In the initial testing of this device, it was noticed that the support balloons lifted the endoscope off of the colon wall, allowing for a reduction in friction. In order to maintain this feature and reduce the amount of tubing required to run along the endoscope, a novel balloon design that provides 360° contact with the colon wall was designed. This new device also had the added benefit of requiring only one air tube per outer balloon. Two of these balloons were added onto the ends of a longer overtube to provide even more support in the turns of the colon. A rendering of this design can be seen in FIG. 4.

Testing

Equipment

The following equipment was used for the second round of testing:

Colon Simulator: To replace the PVC colon simulator, a colonoscopy training model from Kyoto Kagaku in Japan was provided. Improvements over the PVC simulator include: presence of haustral folds throughout the length of the colon; more realistic material characteristics, including flexibility, elasticity, and texture; more realistic support structures; lubrication made specifically for the simulator to help mimic actual conditions in the colon.

Endoscope Simulator: An endoscope simulator consisting of a 4 ft length of insulated power cord and a rounded tip for colon simulator protection was chosen to replace the previous scope simulator. It more closely mimics the flexibility and shape holding characteristics of an actual scope.

Load Cell: Entran ELPM-T2E-25L; Rated for 25 lbs.

Figure 5:
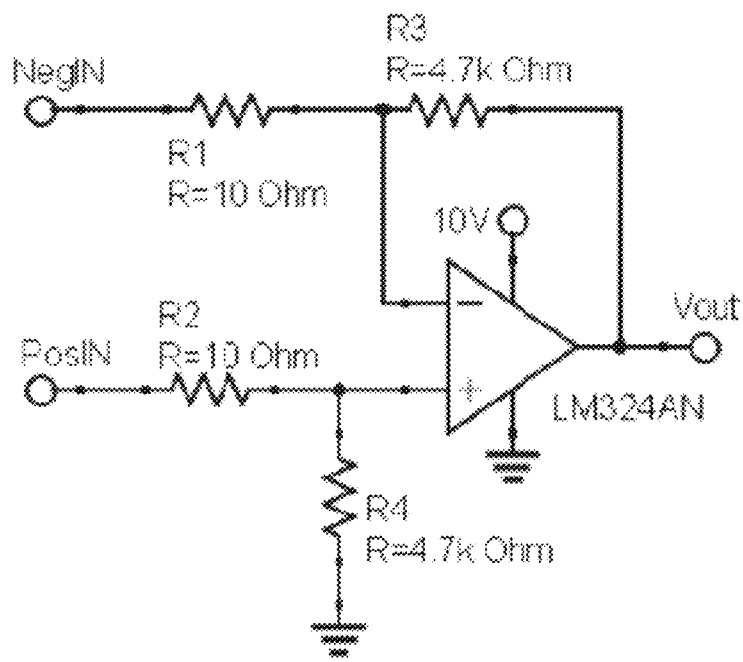
FIG. 5 is an exemplary illustration of a circuit diagram for a differential amplifier.

Differential Amplifier: The maximum output of the load cell was approximately 7 mV. Therefore, a differential amplifier with a gain of 150 was built to improve the resolution of the acquired data. A circuit diagram for this amplifier can be seen in FIG. 5.

Figure 6:
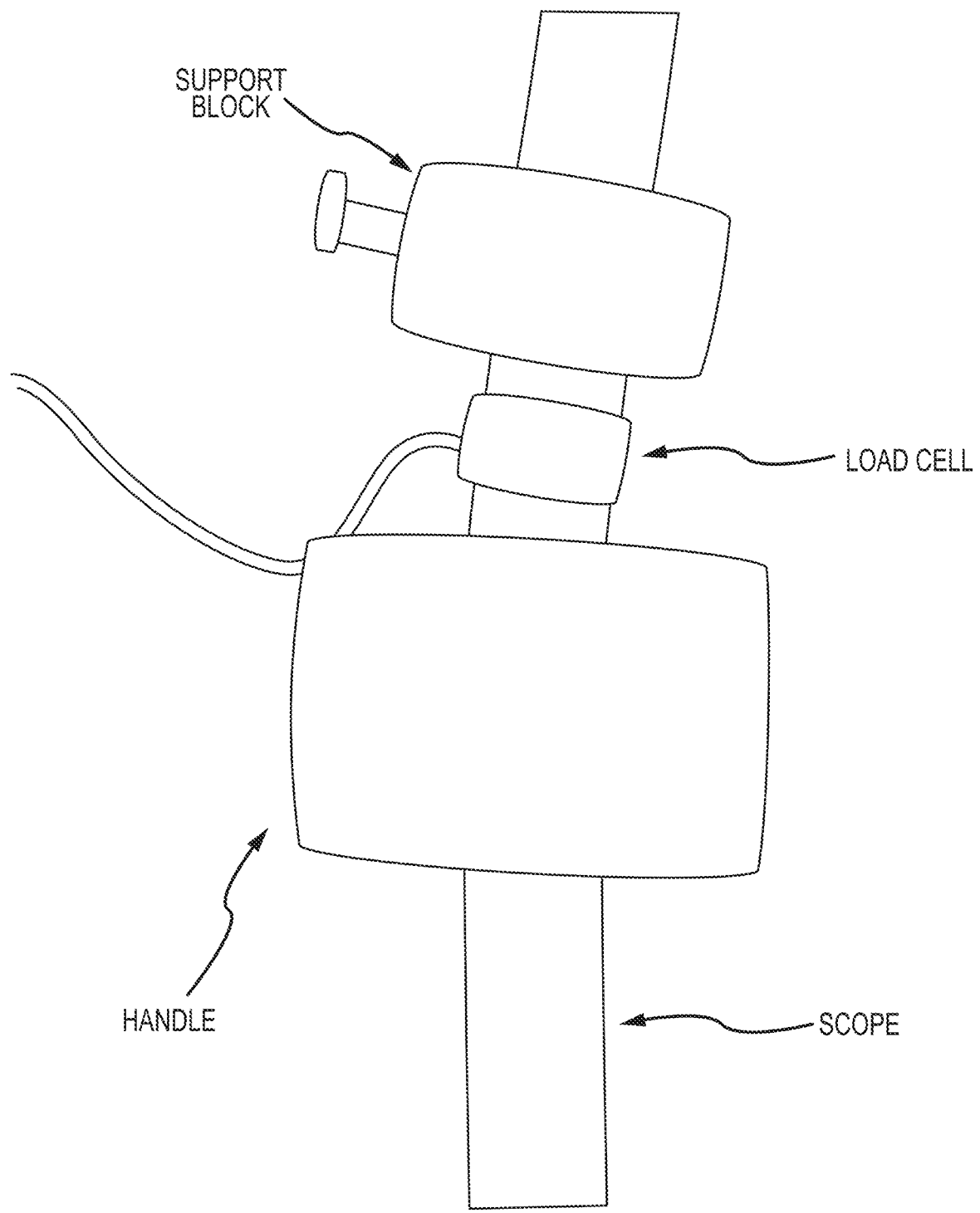
FIG. 6 is an exemplary illustration of a load cell support block and handle used in certain methods of the invention.

Load Cell Support Block and Handle: One end of the load cell is fixed to the scope by a plastic block able to tighten onto the scope. The other end is pressed by a sliding handle to transfer force from the operator's hand to the load cell (FIG. 6).

Figure 7:
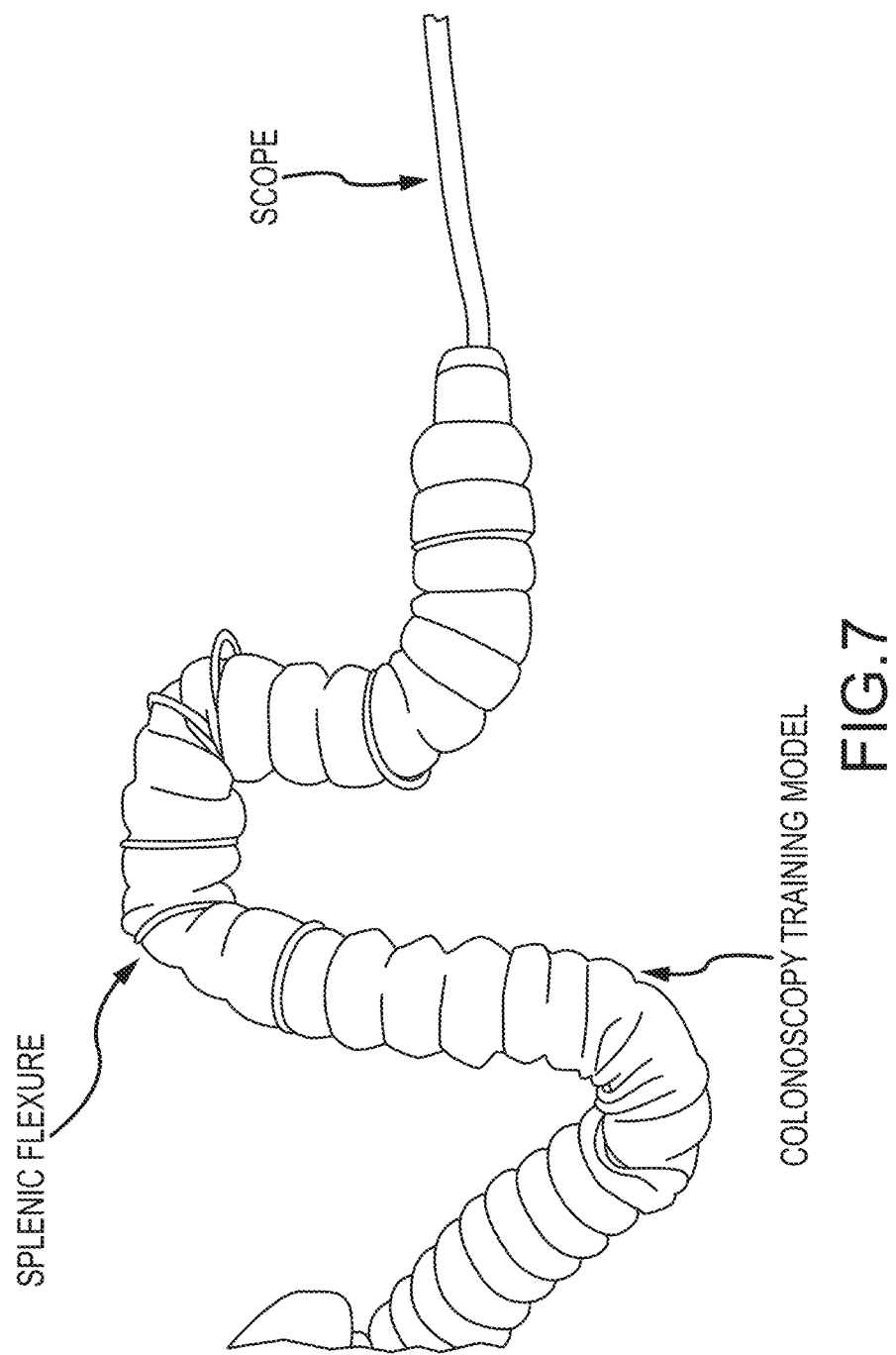
FIG. 7 is an exemplary illustration of a colon simulation configuration.

Procedure:

The following test procedure was executed:

1. Lubrication was prepared and applied to the inside of the colon simulator according to included instructions.
2. The colon simulator was configured to include three 90° turns, each approximately 6 in apart, as shown in FIG. 7 to mimic a typical colon.
3. The forward support block was fixed, with load cell attached, 4 inches from the end of the scope by tightening the screw with a Philips head screwdriver.
4. The endoscope simulator was inserted into the colon simulator until the tip reached 1 inch past the third turn (splenic flexure).
5. If trial included balloon deployment, balloons were deployed in chosen locations.
6. Data acquisition was started in LabVIEW and the scope was pushed with the sliding support block coming into normal contact with the load cell. The scope was advanced at a speed of 1 inch/sec for 12 sec.
7. When data acquisition ended, the created Excel file was saved.
8. Lubrication was reapplied as needed.
9. Steps 4-8 were repeated ten times for each test configuration: plain scope, single balloons (placed individually 1 inch from either side of the center of the first turn in the colon simulator); and joint balloons (balloon segments were centered in the first and second turns of the colon simulator).

Results

Figure 8:
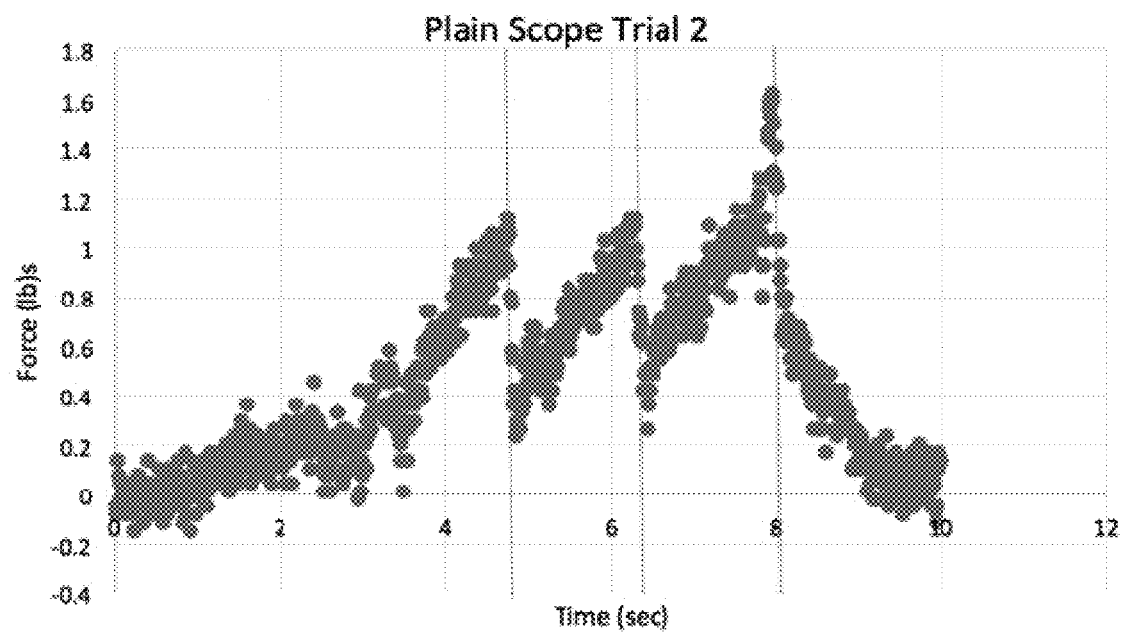
FIG. 8 is a graph illustrating force versus time data for a plain scope test.

FIG. 8 shows the push force (lbf) vs. time (sec) data acquired for one of the trials using the plain scope. A similar trend of gradually increasing force readings with intermittent instances where slipping was observed across all trials, regardless of configuration. The vertical lines indicate where slipping occurred.

Data Analysis

The uncertainty in each force measurement was determined to be u=±0.01 lbf, with the majority of the uncertainty coming from discretization error. This error was lower than in previous testing which could be due to the use of the differential amplifier, making the signal more accurate and easier to read. To analyze the data, the average force applied was calculated for each trial and multiplied by the distance pushed to obtain a measure of total work applied. This was averaged for all trials.

The peak force measured for each test configuration was also averaged over all trials. This data is shown in Table 2. The joint balloons were deployed in corners 1 and 2 of the colon while the separate balloons were just tested in corner 1.

TABLE 2

Average work and peak force applied for each test configuration

| Measurement | Plain Scope | Joint Balloons | Separate Balloons |
|---|---|---|---|
| Average Work (ft-lbf) | 0.63 ± 0.18 | 1.60 ± 0.20 | 0.98 ± 0.14 |
| Average Peak Force (lbf) | 1.60 ± 0.30 | 3.10 ± 0.60 | 1.90 ± 0.30 |

As seen in Table 2, the presence of balloons appears to have increased the necessary push force for endoscope advancement. It is important to note, however, that the application of this data is limited because no tip advancement occurred during the testing. By qualitative observation, it appeared that the presence of joint balloon segments reduced the amount of looping locally, providing additional structure to the part of the colon it was secured in.

Example 4: Testing with Sigmoidscope

Equipment

The following equipment was used for testing: Colonoscopy Training Model (same as in the prior Examples); Sigmoidscope; Load Cell (same as in the prior Examples); Differential Amplifier (same as in the prior Examples); Load Cell Support Block and Handle (same as in the prior Examples).

Procedure

The following test procedure was executed:

1. Lubrication was applied to the inside of the colon simulator according to included instructions.
2. The colon simulator was configured to include three 90° turns, each approximately 6 inches apart, as shown in FIG. 7 to mimic a typical colon.
3. The forward support block, with load cell attached, was fixed 4 inches from the end of the scope by tightening the screw with a Philips head screwdriver.
4. The overtube device was fixed to the scope, approximately 2 inches from the tip so as not to affect articulation.
5. The inner balloon was inflated.
6. Data acquisition was started in LabVIEW and the scope was pushed with the sliding support block coming into normal contact with the load cell. The scope was pushed at a speed of 1 inch/sec for the duration of the test.
7. Once the overtube reaches its desired location, advancement of the scope was stopped. (Desired location could vary depending on the test being performed. Normal deployment location was in the splenic flexure.)

8. The outer balloon was deployed, securing the overtube device to the colon wall.
9. The inner balloon was disengaged, releasing the overtube device from the endoscope.
10. The endoscope was advanced through the colon normally again, until scope reached the end of the colon simulator.
11. When data acquisition ended, the created Excel file was saved.
12. The outer balloon was deflate and the inner balloon was inflated.
13. The scope and attached overtube device were removed from the colon simulator.
14. Lubrication was reapplied as needed.
15. Steps 4-14 were repeated ten times for each test configuration: plain scope; balloon attachment (deployed in splenic flexure).

Results

The overtube device provided reduction in the push force applied. Data for average forces, both peak and overall, are reported in Table 3. All measurements recorded in this table were made as the tip of the scope advanced through the splenic flexure—either as a standalone scope or with a balloon attachment.

TABLE 3

Average peak and overall force applied for each test configuration.

| Measurement | Plain Scope | Balloon Attachment |
|---|---|---|
| Average Peak Force (lbf) | 1.90 ± 0.50 | 1.50 ± 0.30 |
| Average Overall Force (lbf) | 1.18 ± 0.16 | 1.16 ± 0.19 |

Aside from the quantitative data that was collected, once the balloons were deployed from the overtube device, the scope was able to be advanced much more easily than before. The colon simulator also showed less signs of deformation and stretching during tests where the overtube device was deployed.

Data Analysis

A one-tailed t-test was conducted at a 5% significance level:

$$H_0: F_{peak;plain} \leq F_{peak;balloon}$$

$$H_1: F_{peak;plain} > F_{peak;balloon}$$

These tests suggest that supporting the splenic flexure with a further improved balloon attachment reduces the push force necessary for advancement.

Design

Figure 9:
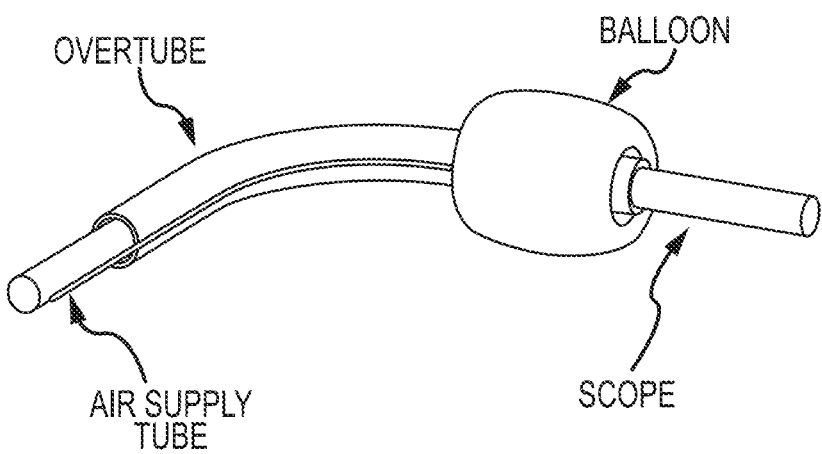
FIG. 9 is an exemplary illustration of an overtube-balloon design.

After the last round of testing, a working design was finalized. An exemplary device comprises an overtube device similar to what was used in the previous round of testing, except it only has a single latex balloon at the front of the over tube. In certain embodiments, the balloon on the back of the device has moderate contribution to keeping the device in place in the colon. A rendering of the device can be seen in FIG. 9.

The overtube device was secured to the scope using a custom inflatable LDPE balloon design team. The latex balloons are made using a custom process described elsewhere herein. This allowed for a more uniform inflation and a cleaner seal.

In order to inflate these two balloons, a syringe pump was used. This syringe pump comprised two linear actuators, powered by an Arduino, and three syringes. Two of the syringes were 60 mL syringes and used to inflate the outer latex balloon, while the third syringe was a 30 mL syringe, and used to inflate the inner LDPE balloon. The whole pump assembly was contained in an acrylic box and activated using a foot pedal switch. This allows for easy use by the doctor. A detailed manufacturing and testing plan can be found elsewhere herein.

Current estimates show that the manufacturing and assembly costs for the devices of the invention would be approximately $10-$15. The anticipated cost for manufacturing the inflation system is about $200. A conventional colonoscopy with biopsy costs $2,070—this does not include higher costs for patients with complications. In some cases, double balloon enteroscopy (DBE) has been used for more complicated colonoscopies ($2,407). DBE is not widely used, includes substantial support equipment, and does not allow for third party scope use—thus preventing wider adoption due to large capital investment. Instead, the present devices can be used with any scope, have little support equipment, and when combined with conventional colonoscopy ($2,070+$200) would cost 10% less than DBE. Current estimates show approximately 15 million colonoscopies annually in the U.S. with this number rising as the population ages.

Example 5: Manufacturing

The fabrication was split into two main systems—the support balloons/overtube device (goes inside the body) and the air supply system (remains outside the body). The parts used for both systems are listed below.

Support Balloons: ¾ inch D PE Corrugated Overtube (McMaster Carr); Latex for balloons (Textile Rubber & Chemical Co, Inc. Fall River, Mass.); ⅛ inch OD PVC Tubing (McMaster Carr); Adhesives and sealants (Locktite Vinyl Adhesive, Elmers Rubber Cement).

Syringe Pump Housing: 5 Sheets×¼ inch thick Clear Cast Acrylic (Colorado Plastics); 1 Sheet×½ inch thick Clear Cast Acrylic (Colorado Plastics); 7 Delrin Blocks of Various Sizes (Colorado Plastics); 2 Black Acrylic Plates (Colorado Plastics); 30 mL Syringe; 2×60 mL Syringe.

Overtube Device Assembly

Balloon Manufacturing

In order to create balloons of specific dimensions to add to the overtube assembly, the balloons were created according to the following procedure:

Liquid Latex

1. Mix natural latex with D710 curing agent in a ratio of 1 kg to 21 g to fill a container.
2. Add dye if desired.
3. Shake and let stand for 12 hrs to eliminate bubbles.

Outer Latex Balloon Procedure

Figure 10A:
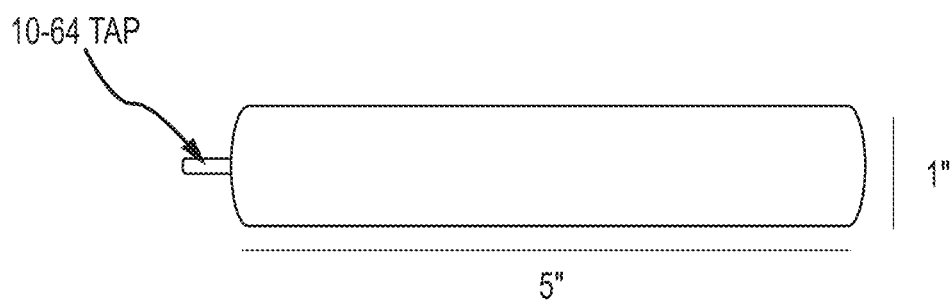
FIG. 10A illustrates steps 1-2 of the outer latex balloon procedure.
Figure 10B:
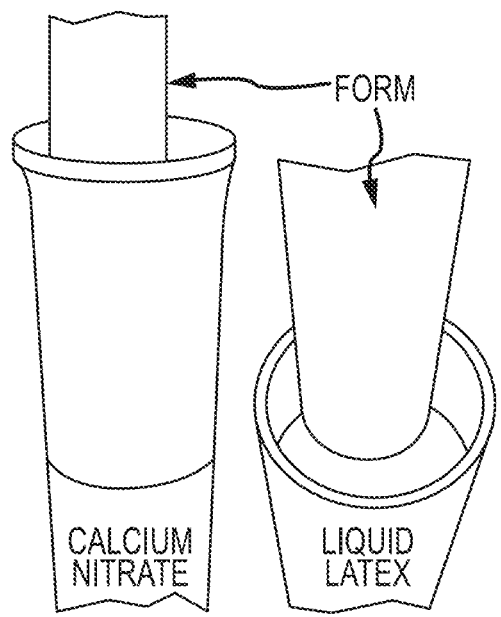
FIG. 10B illustrates steps 4-5 of the outer latex balloon procedure.
Figure 10C:
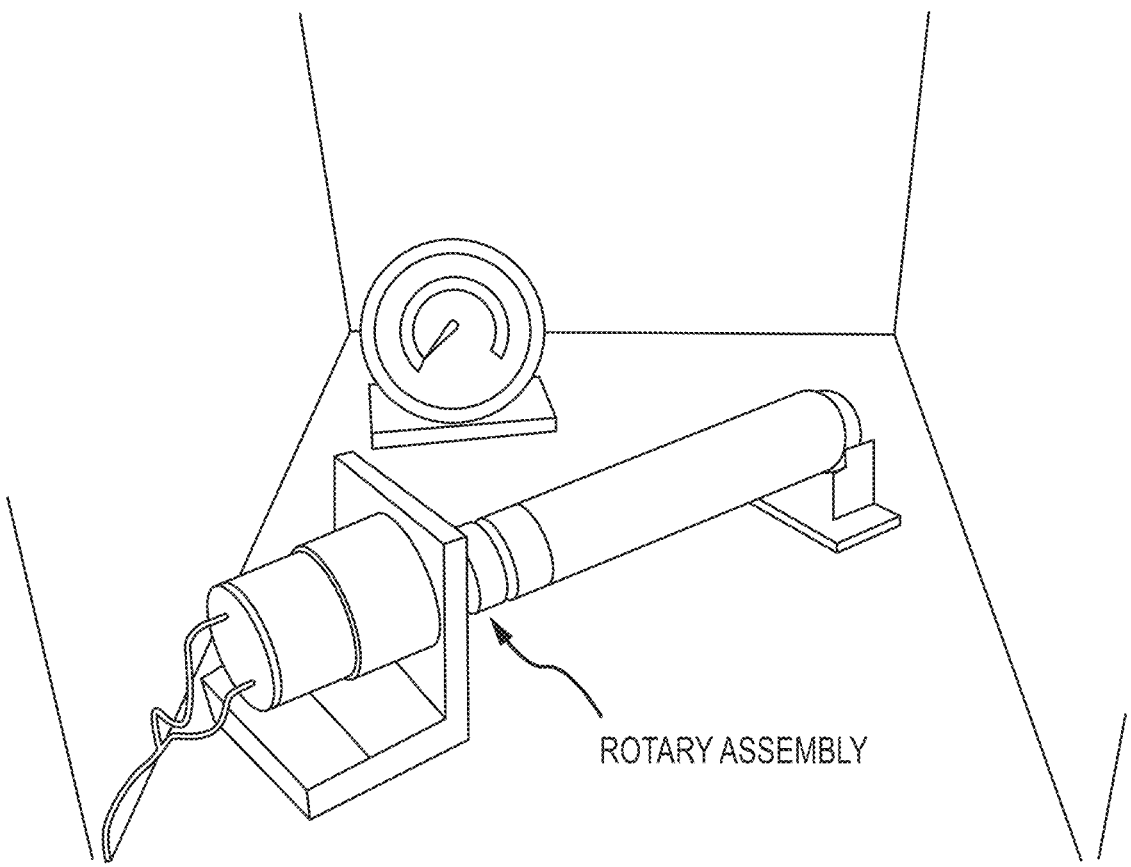
FIG. 10C illustrates step 8 of the outer latex balloon procedure.

1. Machine cylindrical aluminum form to dimensions of 1.00 in D and 5.00 in L (FIG. 10A).
2. Tap a 10-64 hole in the center of one end of the rod (FIG. 10A).
3. Clean with water and sonicate the form for 60 min.
4. Using the plunger device, dip form in calcium nitrate for a dwell time of 5 sec, hang dry for 10 min (FIG. 10B).
5. Using the plunger device, dip form in liquid latex for a dwell time of 45 sec, hang dry for 15 min (FIG. 10B).
6. Dip in distilled water.
7. Remove ½ inch of material from hanging end of form.
8. Bake in oven on rotary assembly for 1 hr at 1000° C. (FIG. 10C).

Figure 10D:
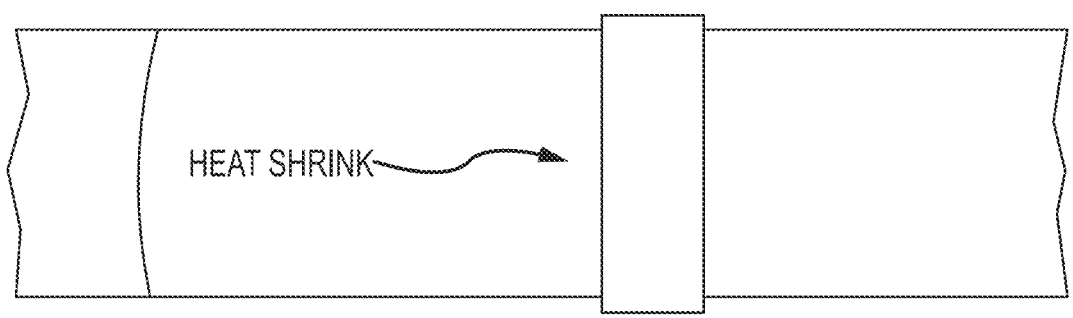
FIG. 10D illustrates step 11 of the outer latex balloon procedure.
Figure 10E:
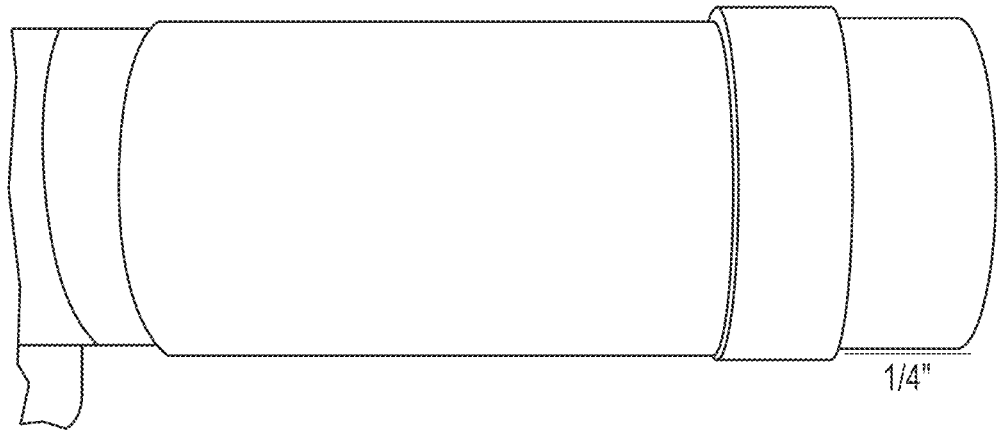
FIG. 10E illustrates step 12 of the outer latex balloon procedure.
Figure 10F:
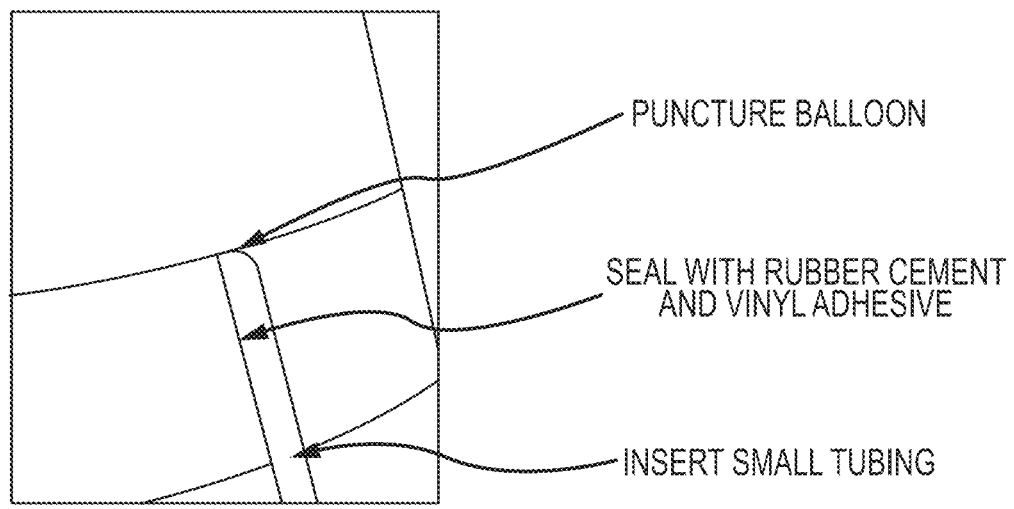
FIG. 10F illustrates steps 17-18 of the outer latex balloon procedure.

9. Cover latex tube in corn starch and remove from form.
10. Coat with corn starch and reattach to form.
11. Add ¼ inch strip of 1 inch diameter heat shrink tubing to center of tube (FIG. 10D).
12. Roll tube back on itself over heat shrink tubing, leaving ¼ inch of tube exposed underneath (FIG. 10E).
13. Hand dip ½ inch of tube in calcium nitrate hold for 5 sec, hang dry for 10 min.
14. Hand dip ½ inch of tube in liquid latex and hold for 30 sec, hang dry for 15 min.
15. Set upright in oven and bake for 1 hr at 1000° C.
16. Coat in corn starch and remove from form.
17. Carefully puncture outer layer and insert air tubing (FIG. 10F).
18. Seal around tubing with rubber cement and vinyl adhesive (FIG. 10F).

Inner LDPE Balloon Procedure

Figure 11A:
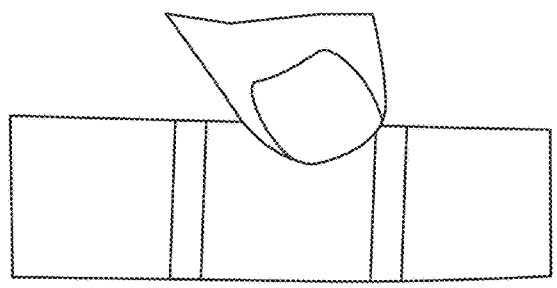
FIG. 11A illustrates step 1 of the inner LDPE balloon procedure.
Figure 11B:
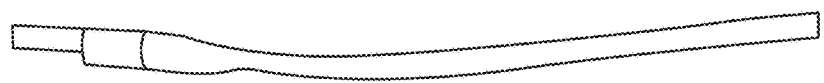
FIG. 11B illustrates step 2 of the inner LDPE balloon procedure.
Figure 11C:
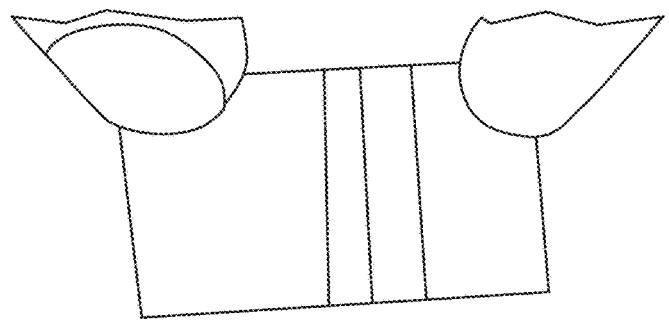
FIG. 11C illustrates step 3 of the inner LDPE balloon procedure.
Figure 11D:
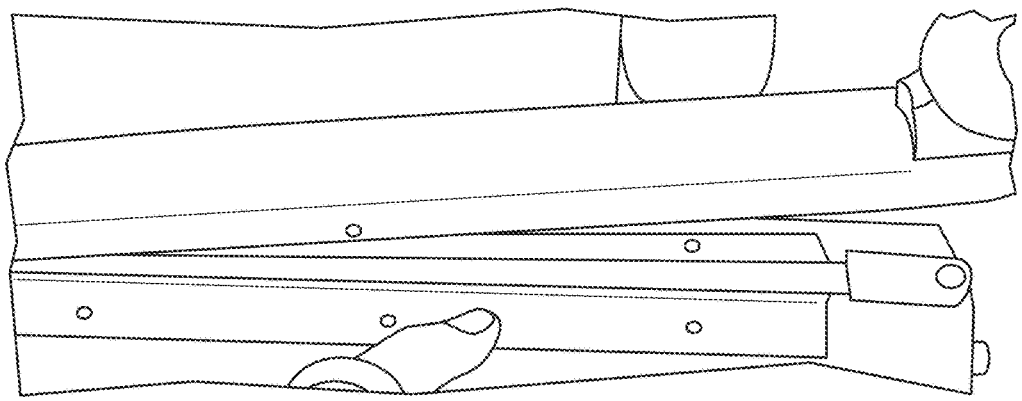
FIG. 11D illustrates step 5 of the inner LDPE balloon procedure.
Figure 11E:
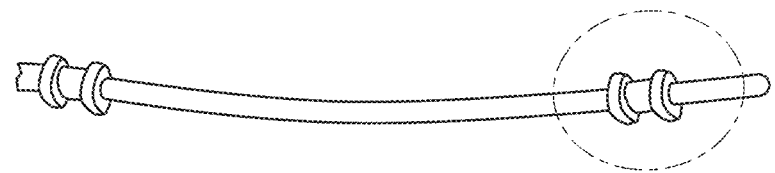
FIG. 11E illustrates step 7 of the inner LDPE balloon procedure.
Figure 11F:
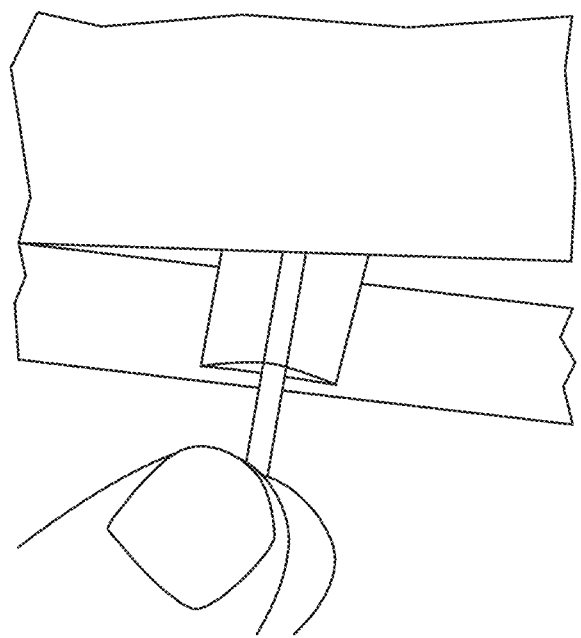
FIG. 11F illustrates step 8 of the inner LDPE balloon procedure.
Figure 11G:
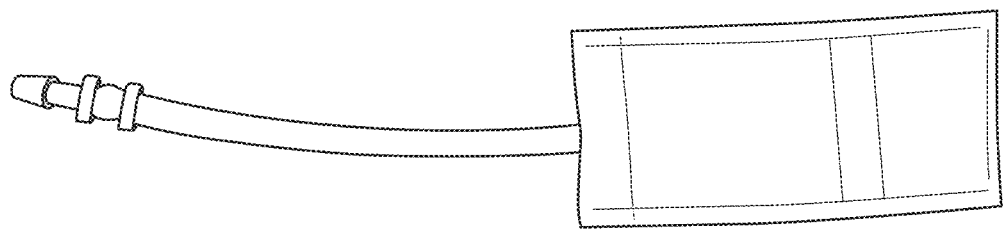
FIG. 11G illustrates a balloon contemplated within the invention.

1. Cut a 4 inch×¾ inch strip of LDPE from an LDPE sheet (FIG. 11A).
2. Cut a 1 inch long piece of heat shrink from a ¹⁄₁₆ inch diameter heat shrink tube (FIG. 11B).
3. Fold the LDPE strip in half to create a 2 inch×¾ inch piece (FIG. 11C).
4. Place one of the 2 inch long sides of the LDPE in the H-190 Uline impulse sealer.
5. Press the sealing arm down and hold for 3 sec (FIG. 11D).
6. Repeat steps 4 and 5 for the other 2 in side of the LDPE balloon.
7. Apply a bead of hot glue to the top and bottom of the heat shrink tube and allow it to dry around the tube (FIG. 11E).
8. Place the open edge of the balloon on the impulse sealer in line with the bead of hot glue and heat shrink tube (FIG. 11F).
9. Press the sealing arm down and hold for three seconds while the edge is sealed, melting the hot glue bead around the heat shrink tubing.

Overtube End Cones

Figure 12A:
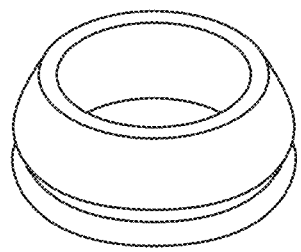
FIGS. 12A-12B illustrate an overtube end cone.
Figure 12B:
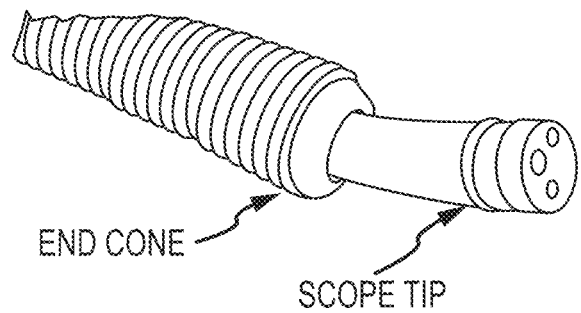

In order to prevent sticking or catching of the overtube as is passes through the colon, end cones were designed to provide a rounded surface between the scope and the overtube (FIGS. 12A-12B). As seen in FIG. 12B, the cone provided a smoother transition area, preventing the region between the scope and the overtube from catching on the haustral folds once inside the colon.

Air Supply System Assembly

Figure 13:
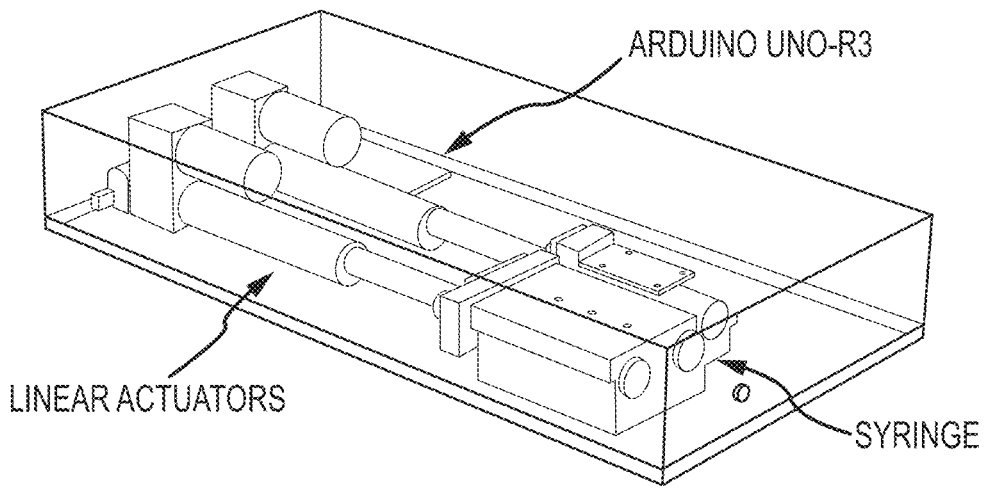
FIG. 13 illustrates a rendering of the air supply system.

For the air supply system housing (FIG. 13), all of the acrylic was cut to size then machined to exact size and necessary holes were drilled. The acrylic was glued together using an acrylic solvent adhesive and put together on a precision ground granite surface using right angle blocks. The delrin blocks were machined to the specifications using mills and attached to the acrylic plate using 10-32 screws. The black acrylic plates were machined using the same mills.

Example 6: Electrical Components

The circuit design of the syringe pump assembly comprised following electrical components:
Arduino UNO R3 (RadioShack, Boulder, Colo.)
SparkFun Ardumoto DC Motor Driver (SparkFun Electronics, Niwot, Colo.)
(2) Concentric International 12V Linear Actuators with Feedback: 4 in Stroke (Pololu Corporation, Las Vegas, Nev.)
Slide Pot—Medium (10 k linear taper) (SparkFun Electronics, Niwot, Colo.)
Amico 220V 10A SPDT Momentary Foot Pedal Switch (Amazon.com, Inc., Seattle, Wash.)
Momentary Toggle Switch (AMTL)
Wagan 5A AC to 12V DC Power Adapter (Amazon.com, Inc., Seattle, Wash.)

Figure 14:
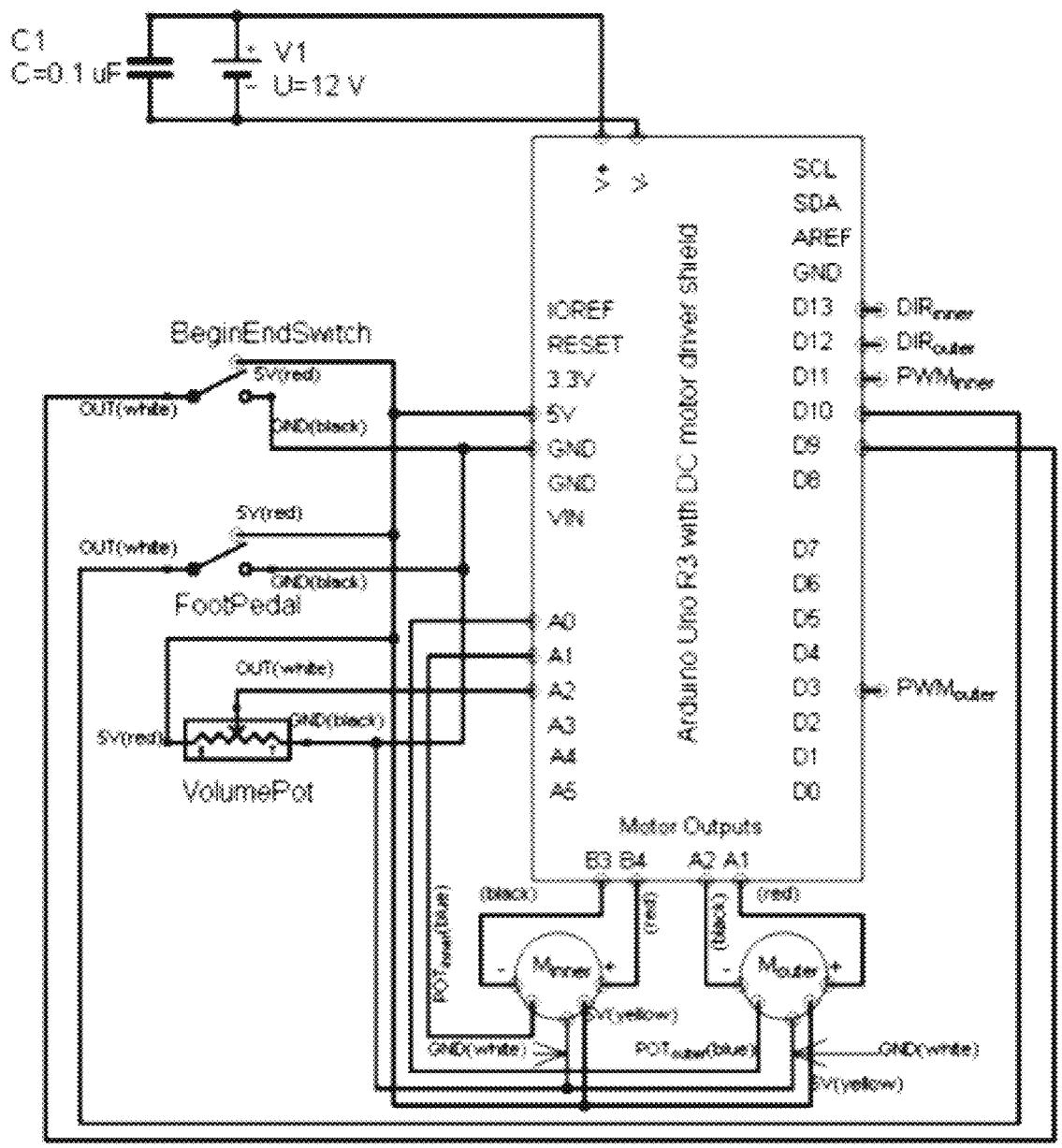
FIG. 14 illustrates a circuit diagram of the syringe pump circuit design.
Figure 15:
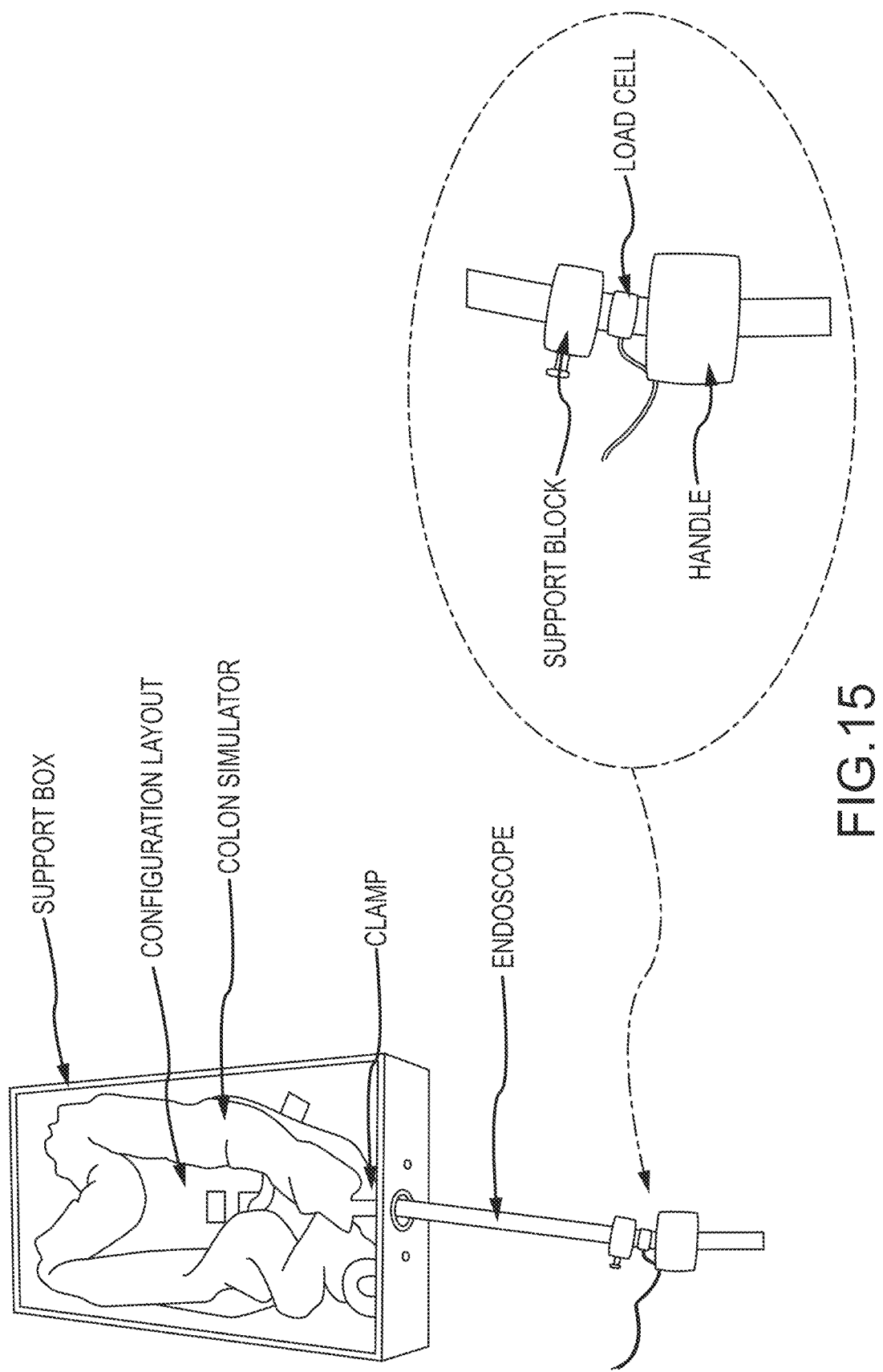
FIG. 15 illustrates an overtube device test setup.

FIG. 14 shows a schematic of the syringe pump circuit design.

Example 7: Systems Implementation

In order to ensure the proper and safe functioning of the syringe pump assembly, an electric motor driving system was created using potentiometers built into the linear actuators. The linear actuators are rated at 35 lbf; therefore, precautions were necessary to avoid actuators extending beyond their stroke limits and potentially damaging other system components. The complete and functioning system must:

Actuate three syringe plungers with the proper stroke length to inflate two balloons to proper volumes.
Be controlled by a foot pedal switch used by the gastroenterologist.

The following steps must be taken to develop this system:
1. Assemble the motor driver board and modify motor, switch, and power supply wires to interface with Arduino headers.
2. Write initial test Arduino code to confirm proper functionality of the linear actuators and drive system. This code allows the linear actuators to drive in a 1 inch forward-backward cycle.
3. Mount all of the system components on the base plate and test functionality using the same small-displacement cycle.
4. Write a second iteration of Arduino code to utilize the built-in potentiometer feedback to allow the linear actuators to drive within the necessary stroke length.
5. Include foot pedal switch controls.
6. Perform further testing (explained below) to ensure the proper inflation volume of each balloon.

Algorithm:

In one aspect, the Arduino code is set up to take inputs from the foot pedal or button placed on the system to inflate and deflate the balloons on the device. The code can be written with various options, which can be selected by the user.

In a non-limiting example, the Arduino code is set up so that each press of the foot pedal executes a single step in the process. In one non-limiting step, the internal balloon is inflated. In another non-limiting step, the outer balloon is inflated and the internal balloon is deflated. In another non-limiting step, the outer balloon is deflated and the inner balloon is inflated. In certain embodiments, such set up reduces inputs from the user by combining commands.

In another non-limiting example, the Arduino code is set up so that the system is directed to complete each step separately. In one non-limiting step, the internal balloon is inflated. In another non-limiting step, the outer balloon is inflated. In yet another non-limiting step, the internal balloon is deflated. In yet another non-limiting step, the inner balloon is inflated. In another non-limiting step, the outer balloon is deflated. In certain embodiments, the code includes feedback from one or more mechanical stops in the system design. The potentiometers measure travel of the syringe pump linear actuators and help insure that the pump is not displaced too far. Further, they help measure the volume of air displaced into the balloons. In certain embodiments, the code uses maximum air volumes and inflation/ deflation rates, as prescribed by the user, when determining how fast and how far to actuate the linear actuators.

Syringe Pump Testing Equipment

The following equipment should be used for testing the syringe pump: Syringe pump (2× Concentric LACT4P-12V-5 Linear Actuators; 2×60 mL syringes for inflating the outer balloon; 1×30 mL syringe for inflating the inner balloon; Arduino control board; Various manufactured parts); Air supply tubing; Test balloons made from latex and LDPE, manufactured to mimic the balloons used on the overtube device.
34

Syringe Pump Testing Procedure
1. Attach syringe pump assembly to power source.
2. Affix one end of an air tube to the inner balloon nozzle on the syringe pump, and the other end to the LDPE test balloon.
3. Inflate the LDPE balloon by pressing the balloon foot pedal switch.
4. Inspect the LDPE balloon for any leaks.
5. Allow the LDPE balloon to stay inflated for 5 min to ensure seal integrity.
6. Deflate the LDPE balloon by pressing the balloon foot pedal switch.
7. Detach air supply tube from the syringe pump and LDPE test balloon.
8. Affix one end of an air tube to the outer balloon nozzle on the syringe pump, and the other end to the latex test balloon.
9. Inflate the latex balloon by pressing the balloon foot pedal switch.
10. Inspect the latex balloon for any leaks.
11. Allow the latex balloon to stay inflated for 5 minutes to ensure seal integrity.
12. Deflate the latex balloon by pressing the balloon foot pedal switch.
13. Detach air supply tube from the syringe pump and latex test balloon.

Overtube Device Testing Equipment

The following equipment should be used for testing the overtube device: Overtube Device (6 inch long corrugated nylon tubing; Latex outer balloon; LDPE inner balloon; Air supply tubing); Colonoscopy Training Model (same as described elsewhere herein); Sigmoidscope; Load Cell (same as described elsewhere herein); Differential Amplifier (same as described elsewhere herein); Load Cell Support Block and Handle (same as described elsewhere herein).

Overtube Device Testing Procedure
1. Prepare lubrication and apply to the inside of the colon simulator according to included instructions.
2. The colon simulator is configured to include three 90° turns, each approximately 6 inch apart, as shown in FIG. 7 to mimic a typical colon.
3. Fix the forward support block, with load cell attached, 4 inch from the end of the scope by tightening the screw with a Philips head screwdriver.
4. Fix overtube device to the scope, approximately 2 inch from the tip so as not to affect articulation.
5. Deploy inner balloon by pressing the foot pedal on the syringe pump, securing the overtube device to the endoscope.
6. Begin data acquisition in LabVIEW and begin to push the scope with the sliding support block coming into normal contact with the load cell. Advance the scope at a speed of 1 inch/sec for the duration of the test.
7. Once the overtube reaches its desired location, stop advancing the scope. (Desired location can vary depending on the test being performed. Normal deployment location is in the splenic flexure.)
8. Deploy the outer balloon by pressing the balloon foot pedal on the syringe pump, securing the overtube device to the colon wall and releasing the overtube device from the endoscope.
9. Begin advancing the endoscope through the colon normally again, until scope reaches the end of the colon simulator.
10. When data acquisition ends, save the created Excel file.
11. Disengage the outer balloon by pressing the foot pedal on the syringe pump, re-inflating the inner balloon.
12. Gently remove the scope and attached overtube device from the colon simulator.
13. Reapply lubrication as needed.
14. Repeat steps 4-13 ten times for each test configuration.

Testing Results

Figure 16A:
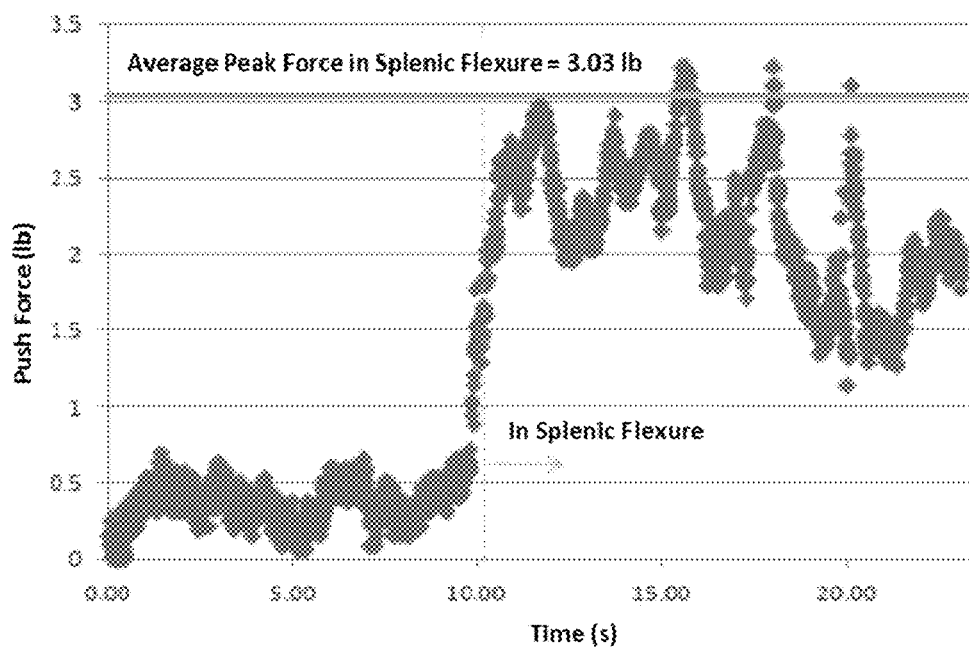
FIGS. 16A-16B illustrate exemplary push force measurements.
Figure 16B:
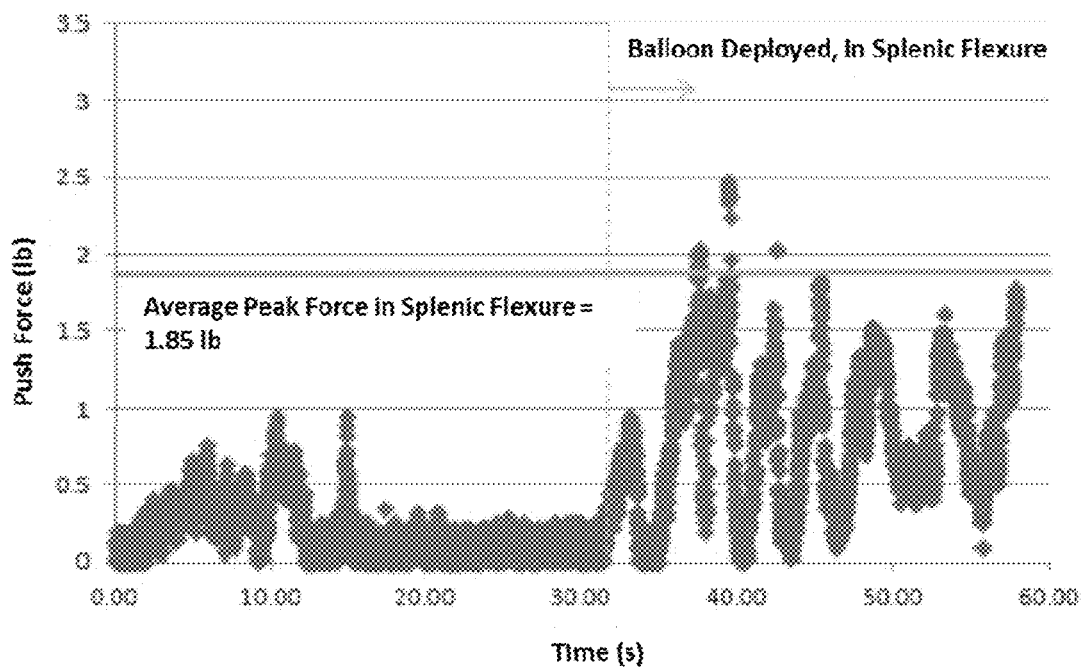

FIG. 16 shows example graphs of force measurement for two different trials that are consistent with overall observations during testing: one with the plain scope, and another with the balloon assembly in use. Note the difference in average peak force in the splenic flexure between these two trials. In the tests using the balloon device, the balloon was deflated until it reached the splenic flexure, at which point it is inflated and the scope is pushed forward and backward to obtain oscillating force measurements. The same method was used to obtain an average peak force calculation.

Figure 17:
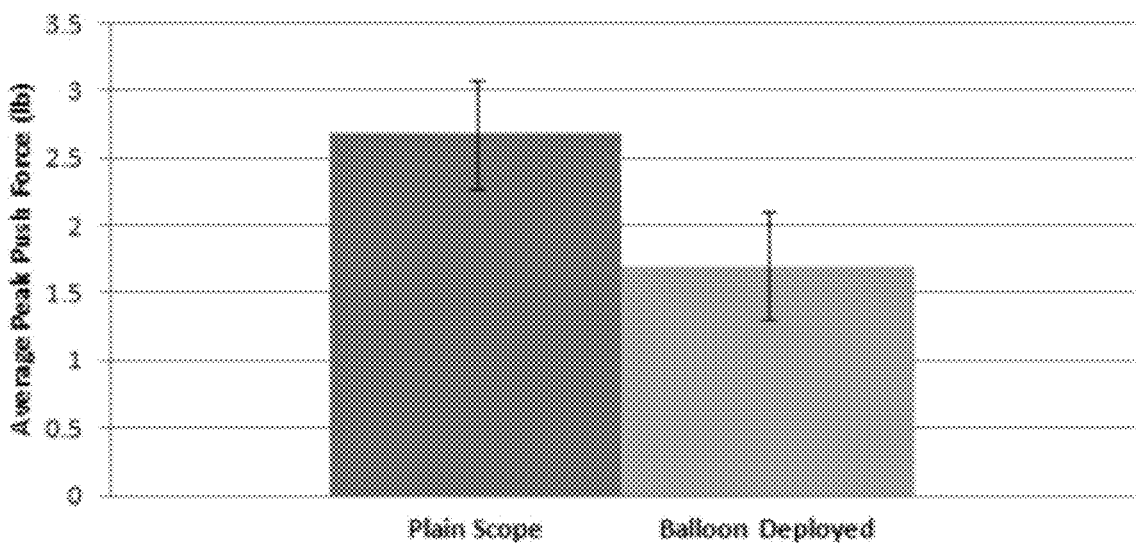
FIG. 17 is a bar graph illustrating the average peak force data.

Table 4 and FIG. 17 show the average peak force measurement data over multiple trials for both the plain scope and scope with the balloon attachment in use. A one-tailed t-test was conducted at a 5% significance level:

$$H_0: F_{peak,plain} \leq F_{peak,balloon}$$

$$H_1: F_{peak,plain} > F_{peak,balloon}$$

This test output a p-value of 0.0001. This means the null hypothesis can be rejected, and thus the peak push force in the splenic flexure was significantly decreased when the balloon assembly was used.

TABLE 4

Average peak push force data comparing the plain scope to the balloons

| Measurement | Plain Scope | Balloon Attachment |
| --- | --- | --- |
| Average Peak Force (lbf) | 2.68 | 1.70 |
| Standard Deviation (lbf) | 0.40 | 0.40 |

Example 8: Instructions for Use

Figure 19A:
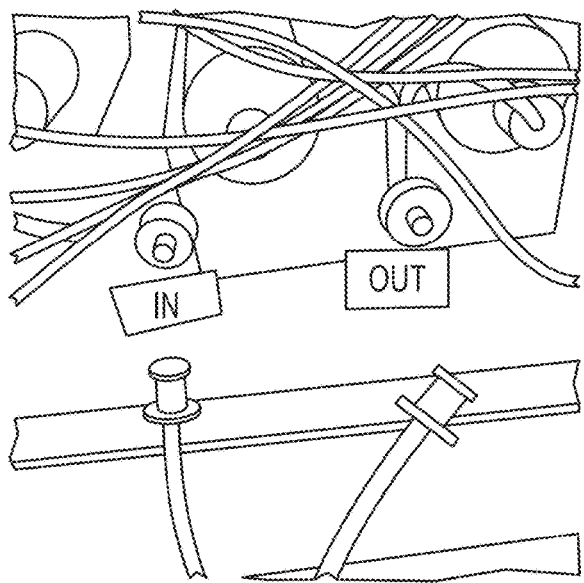
FIGS. 19A-19C illustrate elements of Example 8.
Figure 19B:
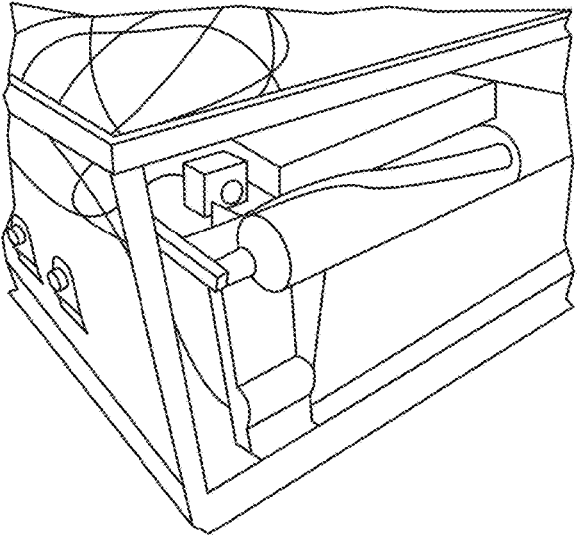
Figure 19C:
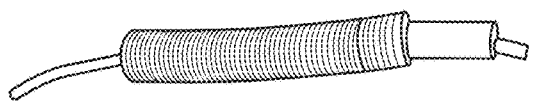

1. Remove the foot pedal from inside the air supply housing.
2. Plug air supply housing into a power outlet.
3. Connect the inner and outer balloon hoses from the overtube device (FIG. 19C) to the labeled connections on the air supply housing (FIG. 19A).
4. Flip the Start switch (FIG. 19B) and check that the inner balloon inflated.
5. Press the foot pedal and check that the inner balloon deflated and the outer balloon inflated.

6. The slide labeled balloon volume (FIG. 19B) can be used to adjust the outer balloon volume before pressing the foot pedal.
7. Flip the start switch again to deflate the balloons on the overtube device.
8. Slide the overtube device onto the endoscope with the tubes pointing away from the tip of the endoscope (FIG. 19C).
9. Adjust the overtube device to just behind the actuating tip of the endoscope and flip the start switch.
10. Check to ensure the overtube device is secured to the endoscope.
11. To deploy the device in the colon when support is needed, press the foot pedal.
12. To deflate the outer balloon and reattach the device to the endoscope press the foot pedal again.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:
1. An endoscopic device comprising:
a flexible overtube, wherein the flexible overtube is configured to be disposed onto an endoscope;
a first inflatable balloon attached to an inner surface of the overtube, wherein, when the flexible overtube is disposed onto the endoscope, the first inflatable balloon is disposed radially inward of the inner surface of the flexible overtube and radially outward of the endoscope; and
a second inflatable balloon attached to an outer surface of the flexible overtube,
wherein, when the flexible overtube is disposed onto the endoscope and the first inflatable balloon is at least partially deflated, the endoscope is longitudinally translatable through the flexible overtube to extend a distal portion of the endoscope beyond a distal extent of the flexible overtube such that the distal portion of the endoscope is external the flexible overtube.

2. The device of claim 1, further comprising the endoscope, wherein the flexible overtube is disposed on the endoscope.

3. The device of claim 1, further comprising a first tubing in fluid communication with the first inflatable balloon and a second tubing in fluid communication with the second inflatable balloon, wherein the first inflatable balloon is inflatable and deflatable by the first tubing, and wherein the second inflatable balloon is inflatable and deflatable by the second tubing.

4. The device of claim 3, wherein at least one of:
(a) the first tubing and the second tubing are attached to one of the outer surface or the inner surface of the flexible overtube;
(b) the first tubing and the second tubing are in fluid communication with at least one pump system;
(c) the first tubing and the second tubing are fillable with a fluid; and
(d) the first tubing and the second tubing are fillable with air.

5. The device of claim 3, wherein the first tubing and the second tubing are in fluid communication with at least one pump system and the at least one pump system is located external the endoscope.

6. The device of claim 1, wherein the first inflatable balloon and the second inflatable balloon are each made of at least one material selected from a group consisting of polydimethylsiloxane (PDMS), LDPE, latex, pebax, silicone, polyethylene terephthalate (PET or PETE), nylon, polyurethane and any other thermoplastic elastomers.

7. The device of claim 1, wherein each of an outer surface of the first inflatable balloon and an outer surface of the second inflatable balloon includes friction elements.

8. The device of claim 7, wherein the friction elements comprise micro-patterned structures.

9. The device of claim 1, wherein at least one of the first inflatable balloon and the second inflatable balloon contain granular packing.

10. The device of claim 9, wherein the at least one of the first inflatable balloon and the second inflatable balloon further contains a fluid.

11. The device of claim 1, further comprising an end cone coupled to a distal end of flexible overtube, wherein, when the flexible overtube is disposed onto the endoscope and the endoscope extends through the flexible overtube, the end cone surrounds at least a section of the outer surface of the endoscope and the end cone is located longitudinally between a distal tip of the endoscope and the second inflatable balloon.

12. The device of claim 1, wherein, when the flexible overtube is disposed onto the endoscope, inflating the first inflatable balloon anchors the overtube to the endoscope.

13. A method of performing endoscopy in a body cavity, the method comprising introducing in the body cavity a distal portion of an endoscopic device, wherein the endoscopic device comprises:
an endoscope;
a flexible overtube disposed over an outer surface section of the endoscope;
a first inflatable balloon attached to an inner surface of the overtube, wherein the first inflatable balloon is disposed radially inward of the inner surface of the flexible overtube and radially outward of the endoscope; and
a second inflatable balloon, wherein the second inflatable balloon is attached to an outer surface of the flexible overtube,
wherein, when the first inflatable balloon is at least partially deflated, the endoscope is longitudinally translatable through the flexible overtube to extend a distal portion of the endoscope beyond a distal extent of the flexible overtube such that the distal portion of the endoscope is external the flexible overtube.

14. The method of claim 13, further comprising, subsequent to introducing the distal portion of the endoscopic device into the body cavity, at least partially deflating the first inflatable balloon and at least partially inflating the second inflatable balloon.

15. The method of claim 13, wherein the endoscopic device further comprises a first tubing in fluid communication with the first inflatable balloon to facilitate at least one of inflation and deflation of the first inflatable balloon and a second tubing in fluid communication with the second inflatable balloon to facilitate at least one of inflation and deflation of the second inflatable balloon.

16. The method of claim 15, wherein at least one of:
(a) the first tubing and the second tubing are attached to one of the outer surface or the inner surface of the flexible overtube;
(b) the first tubing and the second tubing are in fluid communication with at least one pump system; and
(c) the first tubing and the second tubing are independently fillable with air.

17. The method of claim 13, wherein the first inflatable balloon and the second inflatable balloon are each made of at least one material selected from a group consisting of PDMS, LDPE, latex, pebax, silicone, PET, nylon, polyurethane and any other thermoplastic elastomers.

18. The method of claim 13, wherein at least one of the first inflatable balloon and the second inflatable balloon contain granular packing.

19. The method of claim 13, wherein the at least one of the first inflatable balloon and the second inflatable balloon is further fillable with a fluid, wherein the at least one of the first inflatable balloon and the second inflatable balloon adopts a shape of the granular packing when the fluid is removed.

20. The method of claim 13, wherein the device further comprises an end cone coupled to a distal end of the flexible overtube, wherein the end cone surrounds at least a section of the outer surface of the endoscope and wherein the end cone is located longitudinally between a distal tip of the endoscope and the second inflatable balloon.

\* \* \* \* \*